(12) United States Patent
Shirai et al.

(10) Patent No.: US 8,057,456 B2
(45) Date of Patent: Nov. 15, 2011

(54) PANTS-TYPE DISPOSABLE DIAPER

(75) Inventors: Atsuko Shirai, Sakura (JP); Akira Kamori, Sakura (JP); Masamichi Takeda, Sakura (JP)

(73) Assignee: Daio Paper Corporation, Ehime (JP)

( * ) Notice: Subject to any disclaimer, the term of this patent is extended or adjusted under 35 U.S.C. 154(b) by 704 days.

(21) Appl. No.: 11/631,145

(22) PCT Filed: Jun. 30, 2005

(86) PCT No.: PCT/JP2005/012102
§ 371 (c)(1),
(2), (4) Date: Mar. 22, 2007

(87) PCT Pub. No.: WO2006/004002
PCT Pub. Date: Jan. 12, 2006

(65) Prior Publication Data
US 2009/0005751 A1 Jan. 1, 2009

(30) Foreign Application Priority Data

Jun. 30, 2004 (JP) ................. 2004-194522
Nov. 30, 2004 (JP) ................. 2004-346050
Nov. 30, 2004 (JP) ................. 2004-346131
Nov. 30, 2004 (JP) ................. 2004-346139
Jan. 31, 2005 (JP) ................. 2005-023274

(51) Int. Cl.
*A61F 13/20* (2006.01)
(52) U.S. Cl. ......... 604/385.29; 604/385.01; 604/385.02; 604/385.24; 604/385.25; 604/385.26; 604/385.27; 604/385.28; 604/393; 604/394; 604/395; 604/396
(58) Field of Classification Search .......... 604/385.01–385.02, 385.24–385.29, 604/393–396
See application file for complete search history.

(56) References Cited

U.S. PATENT DOCUMENTS 5,817,087 A * 10/1998 Takabayashi et al. ... 604/385.29
(Continued)

FOREIGN PATENT DOCUMENTS

JP 7-265357 10/1995
(Continued)

*Primary Examiner* — Tatyana Zalukaeva
*Assistant Examiner* — Benedict L Hanrahan
(74) *Attorney, Agent, or Firm* — Jordan and Hamburg LLP

(57) ABSTRACT

To prevent a paper diaper reliably from slipping down at a body liquid absorbing time, and to bring the paper diaper into close contact along the line of a body thereby to improve the wearing comfortableness. An armoring sheet includes: waist portion elastic members, and so on; hip surrounding elastic member groups, and so on arranged at the front F and the back B; and a plurality of curved elastic member groups extending, at each of the front F and the back B, from one side jointing edge to the crotch side, reaching the other side jointing edge while passing over the crotch side, and arranged at a spacing without intersecting with each other. The curved elastic member groups have their starting/trailing ends connected at a predetermined spacing substantially over the range from the upper portion to the lower portion of the side portion jointing edge. Moreover, the curved elastic member groups, as arranged on the side of the front F, are given the arrangement pattern, in which the intersection angle on the acute side with the side edge of the absorbent body is 30 degrees or less, and the curved elastic member groups, as arranged on the side of the front B, are given the arrangement pattern, in which the intersection angle on the acute side with the side edge of the absorbent body is 35 degrees or more.

12 Claims, 18 Drawing Sheets

U.S. PATENT DOCUMENTS

| | | | |
|---|---|---|---|
| 6,369,291 B1 * | 4/2002 | Uchimoto et al. | 604/367 |
| 6,602,238 B2 * | 8/2003 | Takei et al. | 604/385.26 |
| 7,449,014 B2 * | 11/2008 | Oba et al. | 604/385.25 |
| 2002/0049421 A1 * | 4/2002 | Hayase et al. | 604/385.27 |
| 2003/0078556 A1 * | 4/2003 | Sasaki et al. | 604/385.25 |
| 2004/0030317 A1 * | 2/2004 | Torigoshi | 604/385.27 |
| 2004/0133180 A1 * | 7/2004 | Mori et al. | 604/385.25 |
| 2005/0004548 A1 * | 1/2005 | Otsubo et al. | 604/385.25 |
| 2008/0027406 A1 * | 1/2008 | Shirai et al. | 604/385.24 |

FOREIGN PATENT DOCUMENTS

| | | | |
|---|---|---|---|
| JP | 7-299094 | | 11/1995 |
| JP | 10-80443 | | 3/1998 |
| JP | 11-36103 | | 2/1999 |
| JP | 2000-14700 | | 1/2000 |
| JP | 2000014700 A | * | 1/2000 |
| JP | 2001-87310 | | 4/2001 |
| JP | 2001-87314 | | 4/2001 |
| JP | 2001087310 A | * | 4/2001 |
| JP | 2001087314 A | * | 4/2001 |
| JP | 2001-204762 | | 7/2001 |
| JP | 2001204762 A | * | 7/2001 |
| JP | 2001-258931 | | 9/2001 |
| JP | 2002-35029 | | 2/2002 |
| JP | 2002-178428 | | 6/2002 |
| JP | 2002-273808 | | 9/2002 |
| JP | 2004-136068 | | 5/2004 |
| JP | 2004136068 A | * | 5/2004 |
| JP | 2004-167043 | | 6/2004 |
| JP | 2004167043 A | * | 6/2004 |

* cited by examiner (DEVELOPED STATE)

(PRODUCT STATE)

(A)

(B)

ADHESIVE SPACING : RUBBER SPACING=1:2

(A)

(B)

54

BACK

56

55

FRONT

PRIOR ART (A)    (B)

PANTS-TYPE DISPOSABLE DIAPER

BACKGROUND OF THE INVENTION

1. Technical Field

The present invention relates to a pants type disposable diaper, which is excellent in a body fit and in a slip prevention, which has a good appearance and which is comfortable to wear.

2. Background Art

In the prior art, the pants type disposable diaper has an elastically extensible member arranged for the nonwoven fabric holding an absorber to absorb a body liquid, thereby to improve the fit on the body.

In Patent Document 1, for example, as shown in FIG. 18, there is disclosed a pants type disposable diaper, which includes a liquid-permeable top sheet 50, a liquid-impermeable back sheet 51, and an absorbent 52 arranged between those sheets 50 and 51. The two side portions of the front and the back are jointed to form a waist opening and a pair of leg openings. The disposable diaper is made to fit the body by arranging waist portion elastic members 48, 48, - - -, and so on along the waist opening, by arranging let portion elastic members 53, 53, - - -, and so on in the two leg openings substantially continuously along the peripheral edges, and by arranging hip portion elastic members 49, 49, - - -, and so on around the waist.

In case the elastic extensible members are arranged individually and independently at the three portions of the waist opening, the leg openings and the hip surrounding, as in the aforementioned disposable diaper, the minimum fit necessary for the paper diaper can be obtained but the satisfaction of the user is not always obtained.

In view of this problem, in Patent Document 2, as shown in FIG. 19, there is disclosed a disposable diaper, which includes a lower curved gather 54 of the trunk gathers as the gather for the abdomen side and/or the back side. The lower curved gather 54 is formed and curved at least to the crotch portion, and has its lowermost portion positioned lower than the uppermost end of the leg openings.

In Patent Document 3, on the other hand, there is disclosed a pants type disposable diaper, as shown in FIG. 20. In this disposable diaper including an absorbent body and an armoring member, first extensible elastic members 55, 55, - - -, and so on and second extensible elastic members 56, 56, - - -, and so on each composed of a plurality of extensible elastic materials are arranged on the front and the back of the armoring member. These extensible elastic members 55 - - - and 56 - - - individually extend from one side edge portion of one of the front and the back through the crotch portion to the other side edge portion, such that at least their portions are arranged along the paired leg surrounding openings and at a predetermined spacing at the crotch portion.

In order to further prevent the slip-down, in Patent Document 4, there is arranged a disposable pants type diaper, as shown in FIG. 21. This diaper is provided with a body, which includes a top sheet, a back sheet and an absorbent. This body is divided into an abdomen side portion and a back side portion. The two right and left side edge portions of the abdomen side portion and the back side portion are jointed and fixed to form a waist opening and leg openings. In the waist opening and the leg openings, there are arranged a waist elastic member 57 and leg elastic members 58, which form gathers substantially continuing along their whole peripheral edge portions. A plurality of hip surrounding elastic members 59, 59, - - -, and so on are arranged on the abdomen side and/or the back side of the hip surrounding elastic members. These hip surrounding elastic members 59, 59, - - -, and so on are arranged in such a displacement to the side of the crotch portion that the displacements of the hip surrounding elastic members 59, 59, - - -, and so on are the largest at the central portion of the abdomen side portion.

In Patent Document 5, moreover, there is disclosed a pants type paper diaper, as shown in FIG. 22. In this pants type paper diaper, elastic ridges 60, 60, - - -, and so on running in the transverse direction are arranged in a gather constitution having no intersection all over the front and the back of the pants. The elastic ridges 60, 60, - - -, and so on of the front and the back are substantially homogeneously arranged in the longitudinal direction on the right and left seal lines, and are more bulged and curved toward the crotch portion as they come closer to the intermediate portion.

Patent Document 1: JP-A-7-265357
Patent Document 2: JP-A-7-299094
Patent Document 3: JP-A-11-36103
Patent Document 4: JP-A-2001-258931
Patent Document 5: JP-A-2001-204762

SUMMARY OF THE INVENTION

We have investigated the elastic member arrangement, which can fit the paper diaper with less physical disorder than that of the prior art and which can prevent the slip-down of the diaper effectively. As a result, we have attained the following knowledge.

(1) For fitting the whole paper diaper on the body having a complicated stereoscopic shape, it is necessary to arrange the elastic extensible members entirely of the diaper thereby to bring the paper diaper into even contact with the body, but not to arrange the elastic extensible members individually and independently on the three portions of the waist opening, the leg openings and the hip surrounding, as disclosed in Patent Document 1.

(2) The front side portion of the body has no bulging portion such as the buttocks unlike the back side of the body, so that the slip-down of the paper diaper has a prominent tendency to occur mainly on the front side.

(3) When the paper diaper is to be fitted on the body, the back side of the body is given a more stereoscopic shape than the front side of the body by the bulge of the buttocks, and has a complicated curved shape. In order to fit the paper diaper without giving the physical disorder to the body, the arrangement pattern of the elastic members has to consider the stereoscopic shape of the buttocks.

(4) The leg surrounding elastic members are arranged substantially along the leg surrounding lines. These leg surrounding elastic members are arranged with a few of elastic extensible members condensed as one bundle (as will be called the "bundled elastic members"), as if they formed one line. Thus, the leg surrounding elastic members bear only a function to clog the clearances between the leg opening edges and the body but do not have the function to hold the absorbent closely on the body.

The aforementioned Patent Documents are considered in view of the points thus far described.

(1) In the disposable diaper according to Patent Document 2, the arrangement of the lower curved gather is expected to prevent the slip-down of the diaper more or less. However, the arrangement of one set of three gathers has a slight effect. Moreover, no device has been made on the body back so that the slip-down prevention and the contact with the body are not sufficiently obtained.

(2) In the case of the disposable diaper according to Patent Document 3, a plurality of elastic extensible members are arranged at a spacing in the crotch portion, so that the leakage prevention at the crotch portion is enhanced. However, the portions, which are clamped by the second extensible elastic members arranged on the back side from one side edge portion of the back through the crotch portion to the other side edge portion and the back side hip surrounding elastic members, are a large area and have no elastic member, so that the absorbent cannot be held in close contact with the body in that area. In the crotch portion, moreover, the first extensible elastic members and the second extensible elastic members are arranged at a predetermined spacing in the longitudinal direction of the diaper, and this shrinking direction of the elastic members arranged in the crotch portion is along the crotch width direction. This raises a problem that the shrinking force to occur in the crotch width direction shrinks the absorber.

(3) In the case of the disposable diaper according to Patent Document 4, the hip surrounding elastic members are arranged in such a curved shape on the abdomen side and/or the back side as are displaced on the side of the crotch portion, so that the component to be generated in the raising direction prevents the slip-down of the paper diaper, thereby to expect a predetermined effect. In order to generate the upward component of the hip surrounding elastic members, however, it is conditioned that the position is strictly fixed at the hip side portions (or the jointing side edges). Since the hip surrounding elastic members are displaced into the curved shape, the downward force acts on the hip side portions to cause the slip-down, if the curved portions of the hip surrounding elastic members are located on the fixed side. As a result, the desired slip-down preventing effect cannot be obtained merely by displacing the hip surrounding elastic members merely into the curved shape. Moreover, the leg surrounding elastic members are arranged linearly in a macroscopic manner along the leg surrounding cut lines, and bear only the function to clog the clearances between the leg opening edges and the body, but not the function to bring the absorbent into close contact with the body. Moreover, the leg surrounding elastic members are arranged to, cross the crotch portion in the widthwise direction, thereby to cause a problem that the extending force to occur in the crotch width direction shrinks the absorbent.

(4) In the disposable paper diaper according to Patent Document 5, it is similar to Patent Document 4 that the hip surrounding elastic members are arranged in the curved shape displaced to the crotch portion sides, but the degree of displacement is different. Specifically, it seems that the curved displacement is made to the crotch portion thereby to give the extensibility to the entire paper diaper. However, the hip surrounding elastic members are displaced in the curved shape, the downward force rather acts on the hip side portions, if the curved portions of the hip surrounding elastic members are at the fixed side, so that the slip-down occurs at the hip side portions.

It is, therefore, a first object of the invention to provide a structure capable of preventing the slip-down of the paper diaper reliably at the time of absorbing a body liquid. A second object is to improve the wearing comfortableness by bringing the paper diaper like shorts or briefs into close contact along the line of the body, so that the absorbent may come into close contact with the body thereby to enhance the leakage-proof effect. A third object is to improve a wearing easiness.

In order to solve the aforementioned problems, according to a first aspect of the invention, there is provided pants type disposable diaper comprising: an absorbent body including an absorbent; and an armoring sheet disposed integrally with the outer face side of the absorbent body, and having a waist opening and a pair of right and left leg openings formed in a product state, when folded at a diaper crotch portion and jointed at its two side portions with the front and the back of the armoring sheet, wherein the armoring sheet includes: waist portion elastic members arranged around the waist opening; a plurality of hip surrounding elastic member groups arranged at the front and the back in the horizontal direction while being vertically spaced; and a plurality of curved elastic member groups extending, at each of the front and the back, from one side jointing edge jointing the front and the back, to the crotch side, reaching the other side jointing edge jointing the front and the back, while passing over the crotch side, and arranged at a spacing without intersecting with each other, and wherein the curved elastic member groups have their starting/trailing ends connected at a predetermined spacing substantially over the range from the upper portion to the lower portion of the front and back jointing edge.

In the first aspect of the invention, especially in the back of the armoring sheet, in addition to the waist portion elastic members and the hip surrounding elastic member groups, there are not provided the bundle-shaped leg surrounding elastic members which are arranged along the leg openings, unlike the paper diaper of the prior art. A plurality of curved elastic member groups extending, at each of the front and the back, from one side jointing edge jointing the front and the back, to the crotch side, reaching the other side jointing edge jointing the front and the back, while passing over the crotch side, and arranged at a spacing without intersecting with each other have their starting/trailing ends connected at a predetermined spacing substantially over the range from the upper portion to the lower portion of the front and back jointing edge.

First of all, in the paper diaper of the invention, the curved elastic member groups are arranged with the starting/trailing ends as the front and back jointing edge, by the elastic members other than the hip surrounding elastic members. As a result, the hip surrounding elastic members and the curved elastic member groups are condensed at high linear density at the jointing edges (as will be called the "side portion jointing edges") between the front and the back, so that the armoring sheet can be strictly fixed by the hip side portions and caused to act the upward force strictly by the curved elastic member groups. As a result, the curved elastic member groups can prevent the paper diaper from slipping down, and can hold the armoring sheet closely on the body. Here, the curved elastic member groups are different in the function and the arrangement mode from the leg surrounding elastic members of the prior art, in that they are not arranged to form a bundle of lines.

According to a second aspect of the invention, there is provided a pants type disposable diaper as in the first aspect of the invention, wherein the curved elastic member groups are arranged at least five each at the front and the back. For providing the slip-down of the paper diaper effectively, it is desired to arrange at least five, preferably seven or more curved elastic member groups.

According to a third aspect of the invention, there is provided a pants type disposable diaper as set forth in the first or second aspect of the invention, wherein, in the jointing edge portion of the front and the back, the elastic member, as positioned closest to the waist opening, of the curved elastic member groups arranged on the front side is spaced at a distance of 20 mm or less from the lowermost one of the waist portion elastic members.

In the third aspect of the invention, in the jointing edge portion of the front and the back, the elastic member, as positioned closest to the waist opening, of the curved elastic member groups arranged on the front side is arranged at a distance of 20 mm or less from the lowermost one of the waist portion elastic members. In short, of the curved elastic member groups, the position of the uppermost elastic member on the side of the jointing portion is arranged rather closer to the waist portion. As a result, when the wearer pulls up the sides of the waist portion, the front side of the paper diaper can be easily pulled upward by the elastic force of the curved elastic members thereby to improve the wearing easiness.

According to a fourth aspect of the invention, there is provided a pants type disposable diaper as set forth in any of the first to third aspects of the invention, wherein, in the jointing edge portion of the front and the back, the elastic member, as positioned closest to the waist opening, of the curved elastic member groups arranged on the back side is spaced at a distance of 20 mm or less from the lowermost one of the waist portion elastic members. In the fourth aspect of the invention, like the third aspect of the invention, when the wearer pulls up the sides of the waist portion, the back side of the paper diaper can be easily pulled upward by the elastic force of the curved elastic members thereby to improve the wearing easiness.

According to a fifth aspect of the invention, there is provided a pants type disposable diaper as set forth in any of the first to fourth aspects of the invention, wherein the arrangement spacing of the curved elastic member groups in the jointing edge portion of the front and the back is made substantially the same as the arrangement spacing of the curved elastic member groups at the crotch portion, and wherein the elastic member, as positioned closest to the crotch side, of the curved elastic member groups is spaced at a distance of ±50 mm or less from the crotch portion folding line of the diaper.

In the fifth aspect of the invention, the arrangement spacing of the curved elastic member groups in the jointing edge portion of the front and the back is made substantially the same as the arrangement spacing of the curved elastic member groups at the crotch portion, and the elastic member, as positioned closest to the crotch side, of the curved elastic member groups is spaced at a distance of ±50 mm or less from the crotch portion folding line of the diaper, that is, the curved elastic member groups bypass the area close to the crotch strictly.

The arrangement spacing of the curved elastic member groups are arranged equivalently at the side jointing edges and at the crotch portion, and the lines drawn by the curved elastic member groups are arranged in the curved shapes of large waves passing over the area near the crotch portion as described above, so that the armoring sheet can be snugly held in close contact with respect to the body.

According to a sixth aspect of the invention, there is provided a pants type disposable diaper as set forth in any of the first to fifth aspects of the invention, wherein the curved elastic member groups arranged on the side of the back are biased at the crotch portion to the front with respect to the crotch portion folding line of the diaper.

In the sixth aspect of the invention, the curved elastic member groups arranged on the side of the back are biased at the crotch portion to the front with respect to the crotch portion folding line of the diaper. It is possible to eliminate the slip-down of the paper diaper, as might otherwise be caused on the side of the buttocks, and to eliminate the slackness of the armoring sheet at the buttocks thereby to fit the paper diaper on the body.

According to a seventh aspect of the invention, there is provided a pants type disposable diaper as set forth in any of the first to sixth aspects of the invention, wherein the curved elastic member groups arranged on the front side are given, at the intersecting portion with the side edge of the absorbent body, an intersection angle on the acute angle side between the curved elastic member groups and the absorbent body side edge is 30 degrees or less, and wherein the curved elastic member groups arranged on the back side are given, at the intersecting portion with the side edge of the absorbent body, an intersection angle on the acute angle side between the curved elastic member groups and the absorbent body side edge is 35 degrees or more.

In the seventh aspect of the invention, the arrangement pattern of the curved elastic member groups on the side of the front and the arrangement pattern of the curved elastic member groups on the side of the back are made different. Specifically, the curved elastic member groups arranged on the front side are given, at the intersecting portion with the side edge of the absorbent body, the intersection angle on the acute angle side between the curved elastic member groups and the absorbent body side edge is 30 degrees or less, and the curved elastic member groups arranged on the back side are given, at the intersecting portion with the side edge of the absorbent body, an intersection angle on the acute angle side between the curved elastic member groups and the absorbent body side edge is 35 degrees or more.

The front side portion of the body does not have such a bulge unlike the back side of the body as provides a hook such as the buttocks. As a result, the slip-down of the paper diaper has a tendency to occur mainly and promptly on the side of the front so that the elastic member groups are arranged at a relatively sharp angle of inclination. If the inclination angle $\theta$ is 30 degrees, therefore, the force of 86.6% or more of the applied elastic force can act as the upper force because of cos 30 degrees=0.866, thereby to prevent the slip-down of the paper diaper effectively.

On the back side, on the other hand, the fit on the body is made more important than the slip-down of the paper diaper. In order to fit the armoring sheet on the bulging shape of the buttocks, the elastic member groups are so arranged at a relatively gentle inclination angle that the extending force may act as much as possible in the direction along the bulge of the buttocks. If the inclination angle $\alpha$ is 35 degrees, therefore, the force of 57.4% or more of the applied elastic force can act as the transverse force because of sin 35 degrees=0.574, so that the armoring sheet can be brought so closely on the body as to wrap the buttocks. As a result, the absorbent body 10 is not shrunken on the central side, but is closely fitted on the body thereby to enhance the leakage-proof effect.

According to an eighth aspect of the invention, there is provided a pants type disposable diaper as set forth in any of the first to seventh aspects of the invention, wherein the curved elastic member groups arranged at the front and the back are turned in arcuate curves at the crotch portion or at the passing over portion on the crotch side.

In the eighth aspect of the invention, the curved elastic member groups are turned in arcuate curves at the crotch portion or at the passing over portion on the crotch side. Specifically, the force to act in the widthwise direction of the paper diaper can be minimized by turning the curved elastic member groups in the arcuate curves, thereby to prevent the shrinkage of the absorbent in the widthwise direction.

According to a ninth aspect of the invention, there is provided a pants type disposable diaper as set forth in any of the first to eighth aspects of the invention, wherein the curved elastic member groups are cut and discontinued on the absorbent.

In the ninth aspect of the invention, the curved elastic member groups are cut and discontinued on the absorbent. As a result, it is possible to prevent the shrinkage of the absorbent reliably in the widthwise direction.

According to a tenth aspect of the invention, there is provided a pants type disposable diaper of the ninth aspect of the invention, wherein the curved elastic member groups are cut at positions substantially along the side edge shaping lines of the absorber.

In the tenth aspect of the invention, on the absorbent (but not the absorbent body), the curved elastic member groups are cut and discontinued, and are cut at positions substantially along the side edge shaping lines of the absorber. By changing the cut positions of the curved elastic members according to the side edge shape of the absorbent, more specifically, the tensions of the elastic members are effectively kept, while preventing the shrinkage of the absorbent, so that the absorbent can be held in close contact with the body.

According to an eleventh aspect of the invention, there is provided a pants type disposable diaper of any of the first to eighth aspects of the invention, wherein the curved elastic member groups are fixed in the transverse area on at least the absorbent body by an adhesive so applied at a vertical spacing to the armoring sheet as to form a plurality of rows along the horizontal direction, wherein the ratio between the spacing width of the adhesive and the spacing width in the adhesive spacing width direction between the curved elastic members is set substantially to an integral multiple, and wherein, on the absorbent body, the curved elastic member groups are cut and discontinued on lines along the longitudinal direction of the diaper.

In the eleventh aspect of the invention, under the condition, in which the curved elastic member groups are fixed by the bead application method in the transverse area on at least the absorbent body by an adhesive so applied at a vertical spacing to the armoring sheet as to form a plurality of rows along the horizontal direction, the elastic members are cut so as to prevent the shrinkage of the absorbent. For the cutting operation, the ratio between the spacing width of the adhesive and the spacing width in the adhesive spacing width direction between the curved elastic members is set substantially to an integer. As a result, the intersection points between the curved elastic member groups and the adhesive lines are arranged on the lines along the longitudinal direction of the diaper, so that the fixed points of the curved elastic members are homogeneously arranged when the curved elastic member groups are cut on the absorbent body along the lines in the longitudinal direction of the diaper.

According to a twelfth aspect of the invention, there is provided a pants type disposable diaper as set forth in any of the first to eleventh aspects of the invention, on the absorbent, the hip surrounding elastic member groups are cut and discontinued.

In the twelfth aspect of the invention, on the absorbent, the hip surrounding elastic member groups are cut and discontinued. As a result, it is possible to prevent the shrinkage of the absorbent reliably in the widthwise direction.

According to a thirteenth aspect of the invention, there is provided a pants type disposable diaper as set forth in any of the first to twelfth aspects of the invention, wherein the elastic member closest to the crotch of the curved elastic member groups arranged on the side of the front and the elastic member closest to the crotch of the curved elastic member groups arranged on the side of the back are close to each other but without any intersection at the crotch portion.

In the thirteenth aspect of the invention, the elastic member closest to the crotch of the curved elastic member groups arranged on the side of the front and the elastic member closest to the crotch of the curved elastic member groups arranged on the side of the back are close to each other but without any intersection at the crotch portion. In the crotch portion, therefore, the absorbent body is pushed under a homogeneous pressure into close contact with the body side by the curved elastic member groups, so that the clearance from the body is sealed to exhibit a high leakage-proof effect.

According to a fourteenth aspect of the invention, there is provided a pants type disposable diaper as set forth in any of the first to thirteenth aspects of the invention, wherein the hip surrounding elastic member groups are fixed on the armoring sheet by the adhesive applied to the peripheries of the elastic members, and wherein the curved elastic member groups are fixed in at least the arrangement area of the hip surrounding elastic member groups, without any adhesive applied to the peripheries of the curved elastic members, but at the intersections with the hip surrounding elastic members, with the adhesive applied to the peripheries of the hip surrounding elastic members.

In the fourteenth aspect of the invention, the elastic members are fixed by the control seaming method, in which the hip surrounding elastic member groups are fixed on the armoring sheet by the adhesive applied to the peripheries of the elastic members. On the other hand, the curved elastic member groups are fixed in at least the arrangement area of the hip surrounding elastic member groups, without any adhesive applied to the peripheries of the curved elastic members, but at the intersections with the hip surrounding elastic members, with the adhesive applied to the peripheries of the hip surrounding elastic members. At the side portions of the hip surrounding shearing, in which the elastic members are condensed, therefore, the quantity and range of the adhesive used can be minimized to prevent the setting of the sheet with the adhesive and to give softness.

ADVANTAGE OF THE INVENTION

According to the invention, as has been described in detail, all the elastic members are arranged by using the side jointing edges as the starting/trailing ends so that the fastening forces at the side jointing edges can be set relatively high. As a result, all the elastic members exhibit the extending forces by using the side jointing edges as the fixed points. It is, therefore, to prevent the slip-down of the paper diaper reliably at the time of absorbing a body liquid, to improve the wearing comfortableness by bringing the paper diaper like the shorts or the briefs into close contact along the line of the body and to enhance the leakage-proof effect, and to improve the wearing easiness.

The effects are described more specifically.
(1) The armoring sheet comes as a whole into close contact with the stereoscopic shape of the body. As a result, the absorbent body can come into the close contact with the body thereby to prevent the leakage of the body liquid effectively and to follow the motion thereby to improve the wearing feel.
(2) The pattern, in which the elastic members are partially arranged, as in the prior art, is not adopted, but many elastic members are homogeneously arranged all over. Therefore, the extending force per elastic member can be suppressed small so that the paper diaper can be extended by a smaller force and worn than that of the paper diaper of the prior art.

Moreover, the armoring sheet is not shrunken small when the paper diaper is not worn, so that the diaper can be easily worn without catching the legs.

(3) Unlike the paper diaper of the prior art, the fastening force is not concentrated at the waist portion or the leg surroundings, so that the pressed feel or the trace by the rubber can be eliminated.

BEST MODE FOR CARRYING OUT THE INVENTION

In the following, an embodiment of the present invention is described in detail with reference to the accompanying drawings.

DETAILED DESCRIPTION

First Embodiment

Figure 1:
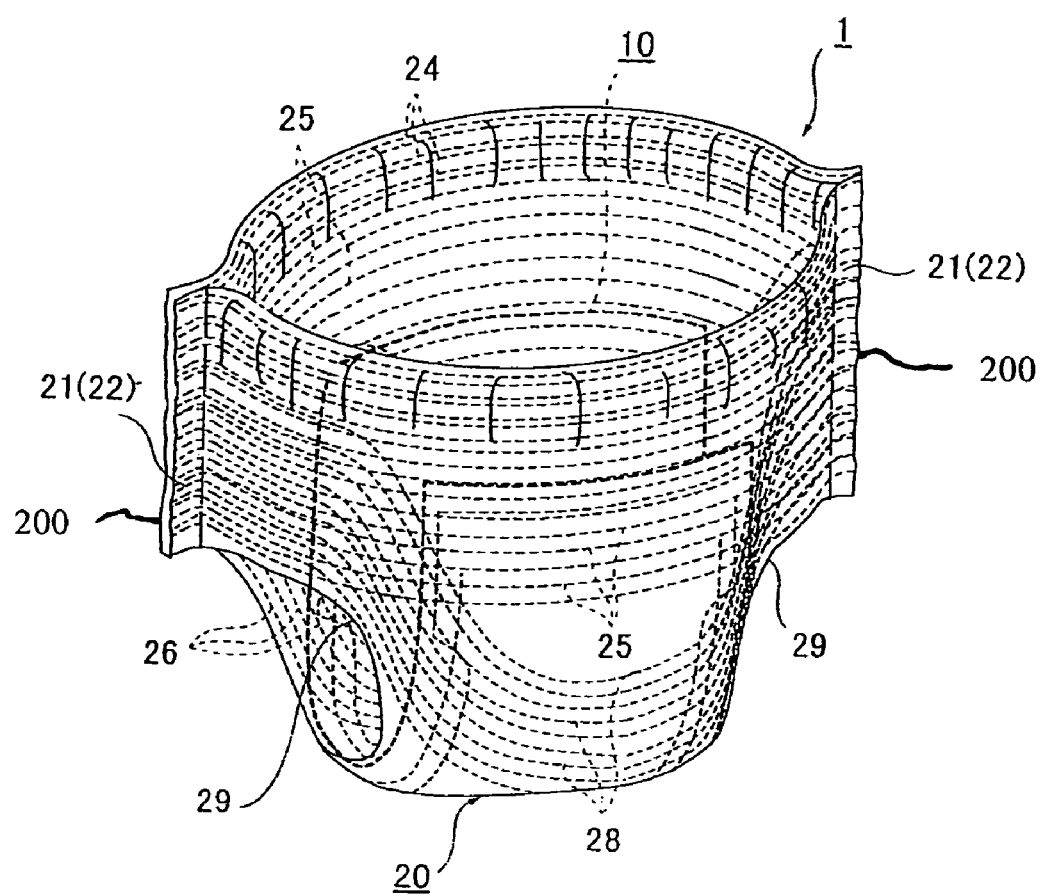
FIG. 1 is an external view of a product state of a pants type disposable paper diaper 1 according to the invention.
Figure 2:
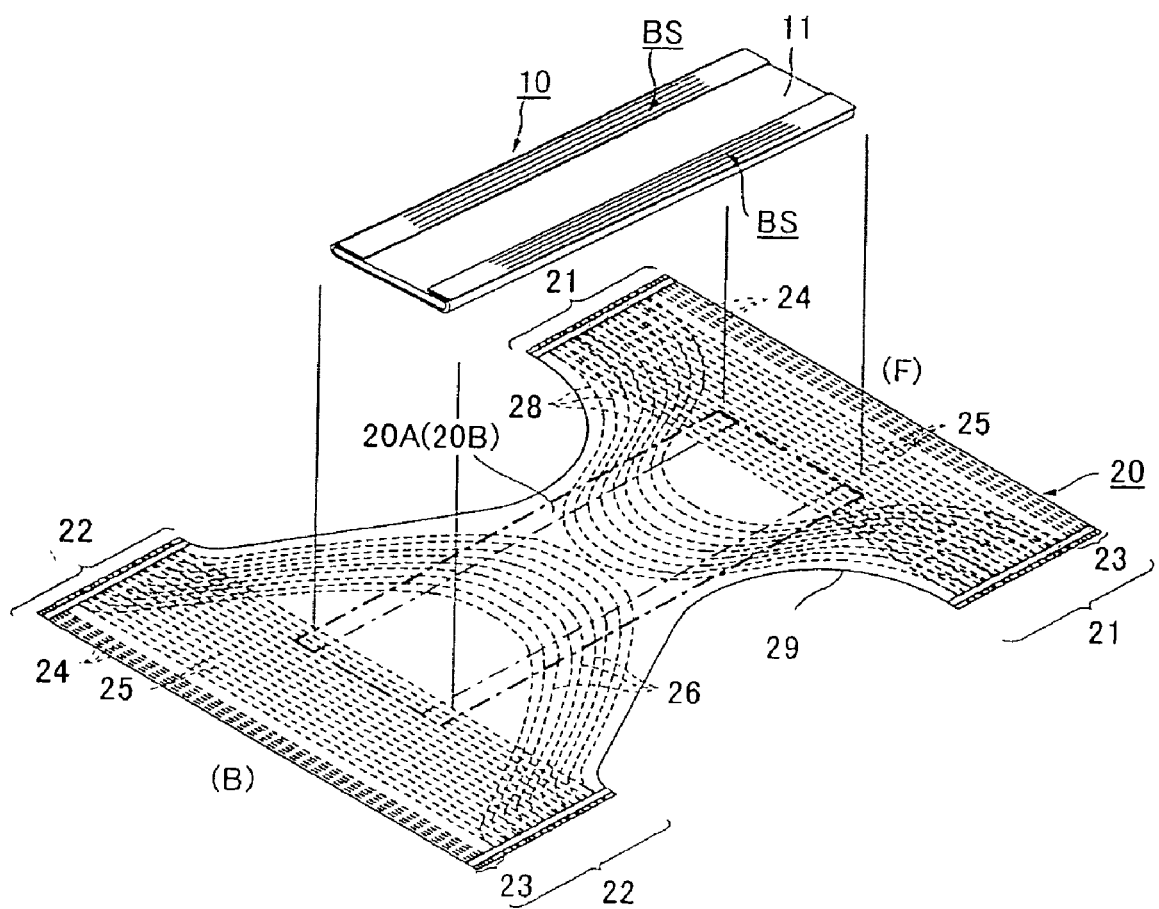
FIG. 2 is an assembly diagram in a developed state.
Figure 3:
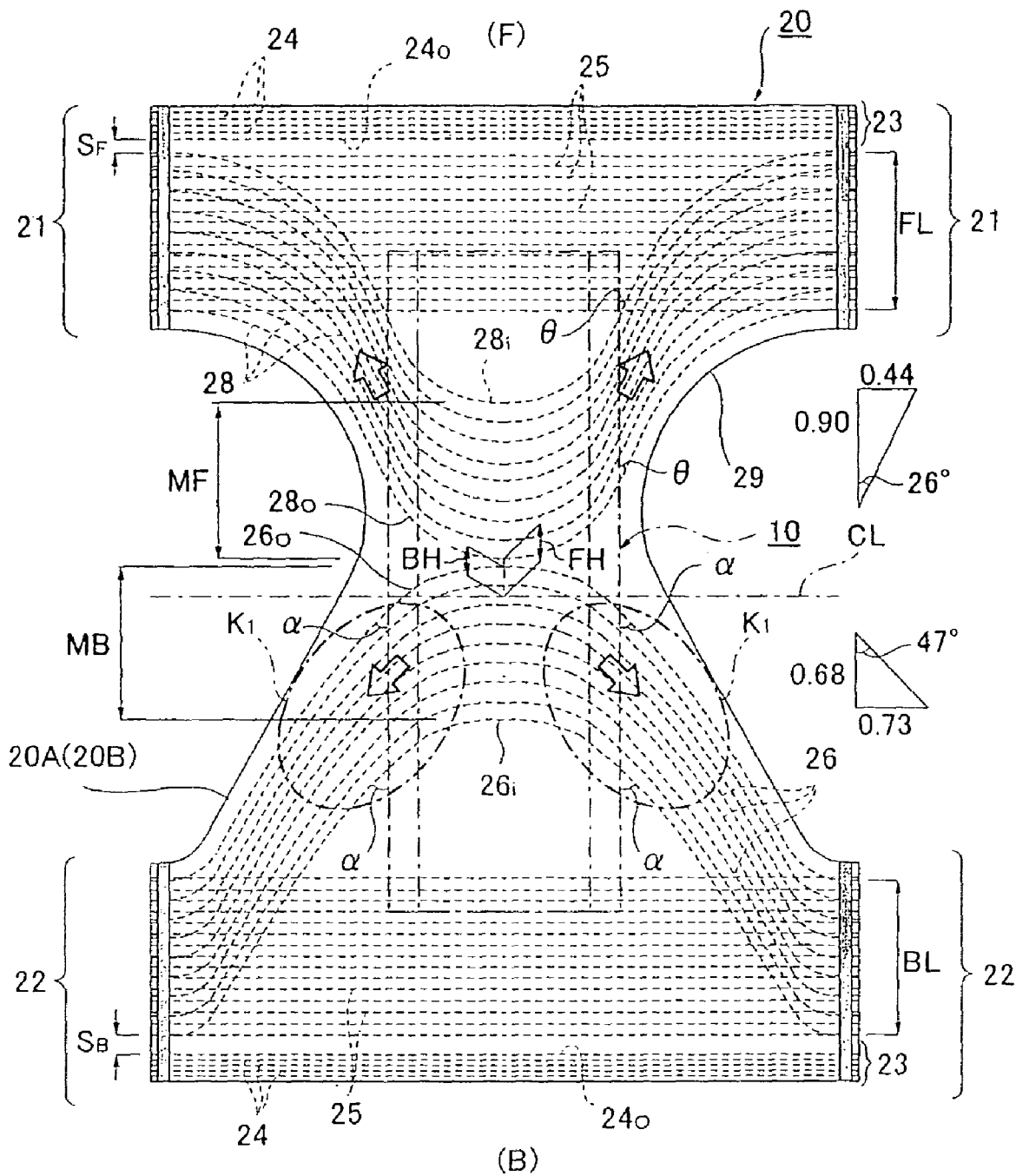
FIG. 3 is a developed diagram of an armoring sheet 20.

FIG. 1 is an external view of a product state of a pants type disposable paper diaper according to the invention; FIG. 2 is an assembly diagram in a developed state; and FIG. 3 is a developed diagram of an armoring sheet.

As shown in FIG. 1 and FIG. 2, the present pants type disposable paper diaper 1 (as will be simply called the "paper diaper") includes an absorbent body 10 having an absorbent 13 such as cotton pulp interposed between a liquid-permeable surface sheet 11 made of nonwoven fabric and a leakage-proof sheet 12 made of polyethylene or the like, and an armoring sheet 20 disposed integrally on the outer face side of the absorbent body 10. The pants type paper diaper is given such a structure in its product state that a waste opening and a pair of right and left leg openings are formed by jointing the front and the back of the armoring sheet 20 on the two side portions to form left and right joined edges 200.

The absorbent body 10, the armoring sheet 20 and their assembled structure are described in the recited order in the following.

(Structure of Absorbent Body 10)

Figure 4:
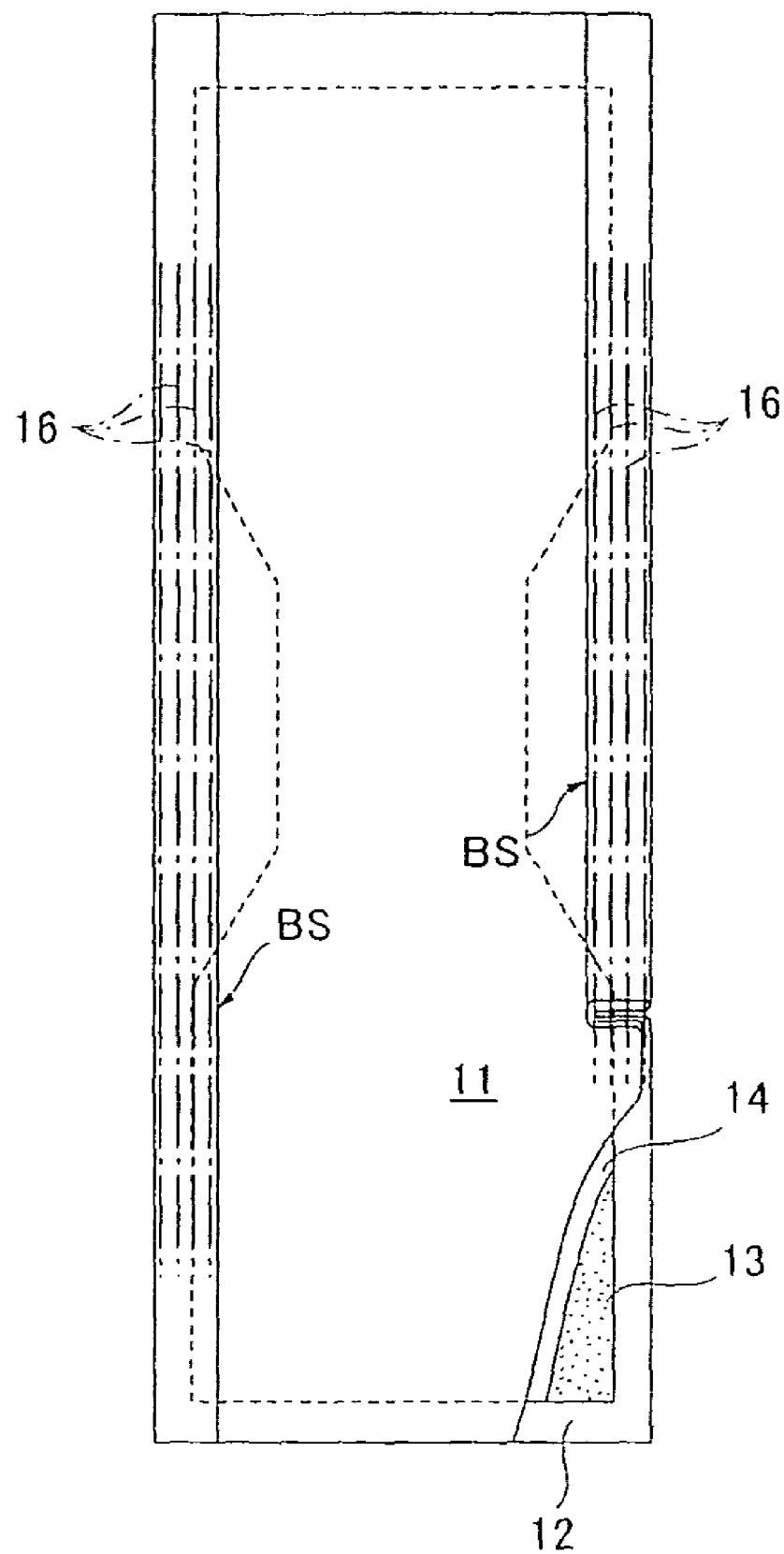
FIG. 4 is a top plan view of an absorbent body 10.

First of all, one example of the structure of the absorbent body 10 is described in detail with reference to FIG. 4 and FIG. 5.

The absorbent body 10 is given a structure, in which the absorbent 13 of cotton pulp is interposed between the liquid-permeable surface sheet 11 of nonwoven fabric or the like and the leakage-proof sheet 12 of polyethylene or the like, and absorbs and hold the body liquid.

The absorbent 13, as used in the shown example, is molded generally into a rectangular shape having such a width size as will not give a stiff feeling to the wearer with the touch on the crotch. This absorbent 13 is so enclosed by crepe paper 14 as to hold its shape and to improve the diffusion of the body liquid having passed through the liquid-permeable surface sheet 11. Here, it is desired that an air-laid absorbent capable of compacting the bulk is used as the absorbent 13.

The liquid-permeable surface sheet 11 for covering the surface side (or the skin touching face side) of the absorbent 13 is suitably exemplified by porous or non-porous nonwoven fabric or porous plastic sheet. The material fibers composing the nonwoven fabric can be exemplified by not only synthetic fibers such as an olefin family, a polyester family or a polyamide family such as polyethylene or polypropylene, but also regenerated fibers such as rayon or cupra, or natural fibers such as cotton. The material fibers may be formed into the nonwoven fabric prepared by a suitable treating method such as the spun lace method, the spun bonding method, the thermal bonding method, the melt blown method or the needle punching method. Of these treating methods, the spun lace method is excellent in the richness of softness and drape characteristics, and the thermal bond method is excellent in bulkiness and softness. The liquid-permeable surface sheet 11 can absorb, in case it is formed with numerous pores, urine or the like promptly so that it is excellent in the dry touching properties. The liquid-permeable surface sheet 11 extends to the back side of the absorbent 13 while enclosing the side edge portions of the absorbent 13.

The leakage-proof sheet 12 for covering the back side (or the skin non-touching face side) of the absorbent 13 is made of a liquid-impermeable plastic sheet of polyethylene or polypropylene. In recent years, however, a moisture-permeable sheet is suitably used in view of preventing the wearer from becoming stuffy. This water shielding moisture-permeable sheet is a microporous sheet, which is prepared by melting and blending an inorganic filler in an olefin resin such as polyethylene or polypropylene to form a sheet and then by stretching the sheet uniaxially or biaxially. This porous film is superior in softness because its rigidity is lower than that of the non-porous sheet having an equal thickness.

Figure 5A:
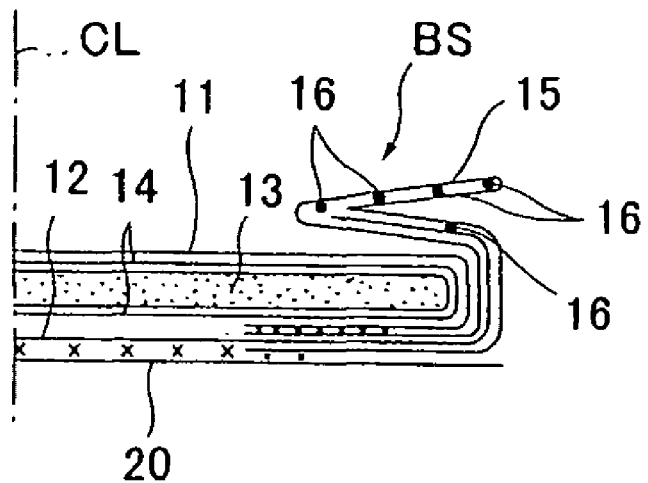
FIG. 5(A) is a transverse section of one half of the absorbent body 10 in a developed state.
Figure 5B:
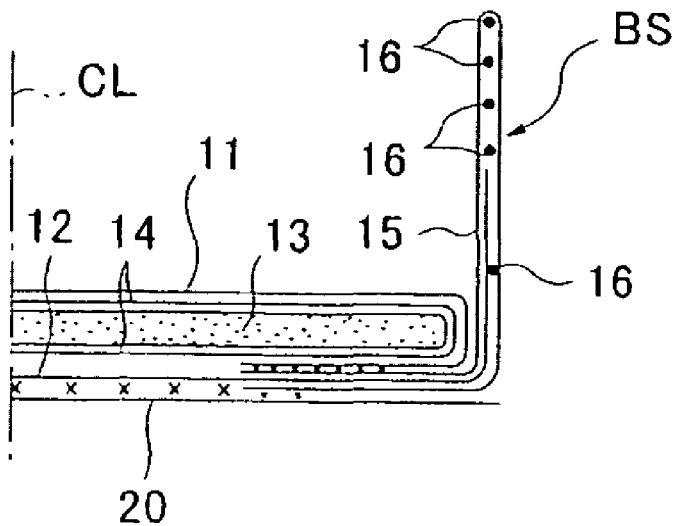
FIG. 5(B) is diagram showing the same in a product state.

On the other hand, a gathered nonwoven fabric 15 for forming a stereoscopic gather BS uses a nonwoven fabric formed into double sheets by folding it back, as shown in FIG. 5, and is extended and adhered to the back side of the absorbent 13 while wrapping the side edge portions of the absorbent 13, as wrapped by the liquid-permeable surface sheet 11, from the upper side. More specifically, the gathered nonwoven fabric 15 is: adhered, in the longitudinal intermediate portion of the paper diaper, with a hot-melt adhesive or the like while leaving the portion to form the stereoscopic gather BS, over the range from the widthwise intermediate portion to the back side of the absorbent 13; and in the longitudinal front and back end portions, at the section from the widthwise intermediate portion to the one side end edge over the range to the back side of the absorbent 13, and at the portion to form the stereoscopic gather BS being folded at the upper face portion of the absorbent 13, with the hot-melt adhesive.

A plurality of filament elastic extensible members 16, 16, - - - , and so on are arranged at the raised leading end side portions in the gathered nonwoven fabric 15 formed of the double-sheet nonwoven fabric. The filament elastic extensible members 16, 16, - - - , and so on are used, in the product state shown in FIG. 5(B), to form the stereoscopic gather BS by raising the nonwoven fabric portion protruded from the absorbent side edge portion by the elastic extending force.

The leakage-proof sheet 12 proceeds into the gathered nonwoven fabric 15 of the double sheet shape thereby to form a leakage-proof wall on the lower end side of the stereoscopic gather BS, as shown in FIG. 5. This leakage-proof sheet 12 is suitably made of an opaque one for preventing the feces or urine from appearing brown. For this opaque sheet, a film is prepared by adding a pigment or filler such as calcium carbonate, titanium oxide, zinc oxide, white carbon, clay, talc or barium sulfate into plastics.

The filament elastic extensible members 16 can be made of a usually used material such as styrene family rubber, olefin family rubber, urethane family rubber, ester family rubber, polyurethane, polyethylene, polystyrene, styrene-butadiene, silicone or polyester. In order not to be seen from the outside, the filament elastic extensible members 16 may have a thickness of 925 dtex or less and a tension of 150 to 350% and may be arranged at a spacing of 7.0 mm or less. Here, the filament elastic extensible members may also be replaced by tape-shaped elastic extensible members having a width.

Like the liquid-permeable surface sheet 11, the material fibers making the gathered nonwoven fabric 15 can also be not only synthetic fibers such as an olefin family, a polyester family or an amide family such as polyethylene or polypropylene, but also regenerated fibers such as rayon or cupra, or natural fibers such as cotton. The material fibers may be formed into the nonwoven fabric prepared by a suitable treating method such as the spun bonding method, the thermal bonding method, the melt blown method or the needle punching method. Especially, the nonwoven fabric to be used may be excellent in air permeability with a reduced Tsubo so as to prevent the wearer from becoming stuffy. Moreover, the gathered nonwoven fabric 15 is desirably made of water-repellent nonwoven fabric coated with a water repellent of a silicone group, a paraffin metal group, an alkyl chromic chloride group for preventing the permeation of urine and for preventing the wearer from getting a rash thereby to enhance the touch feeling (or dry feeling) of the skin.

(Structure of Armoring Sheet 20)

As shown in FIG. 2 and FIG. 3, the armoring sheet 20 is a nonwoven fabric sheet having a two-layered structure composed of an upper-layer nonwoven fabric 20A and a lower-layer nonwoven fabric 20B, and various elastic members are arranged between the upper-layer nonwoven fabric 20A and the lower-layer nonwoven fabric 20B thereby to afford a stretchability. The top plan shape is formed generally into a pseudo-hourglass shape by a recessed leg-surrounding cut line 29 forming leg openings on the two sides at its intermediate portion.

The armoring sheet 20 according to the invention includes, as its elastic members, in the developed shape shown in FIG. 3, waist portion elastic members 24, 24, - - - , and so on, which are arranged in the waist opening surroundings 23, and a plurality of hip surrounding elastic member groups 25, 25, - - - , and so on arranged on the front F and the back B at a vertically spacing and along the horizontal direction. Individually at the front F and the back B, separately of the hip surrounding elastic member groups 25, 25, - - - , and so on, there are further included a plurality of curved elastic member groups 26 - - - , and 28 - - - , which extend to the crotch side from the one-side joint edge jointing the front F and the back B thereby to reach the other side joint edge of the front and the back while passing over the crotch and which are arranged at a spacing to have no intersection with each other. Here, this armoring sheet 20 is not provided with the so-called "leg surrounding elastic members", which continue substantially along the leg-surrounding cut line 29.

The foregoing various elastic members are individually described in detail in the following.

The waist portion elastic members 24, 24, - - - , and so on are a plurality of threads of rubbery elastic members, which are arranged vertically at a spacing near the waist opening edges in the ranges of side jointing edges 21 and 22, at which the front F and the back B are jointed. The waist portion elastic members mount the paper diaper on the body by applying the shrinking forces to fasten the waist portion of the body. The waist portion elastic members 24 employ the rubbery threads in the shown example, but may use tape-shaped shrinking members.

The hip surrounding elastic member groups 25, 25, - - - , and so on are elastic members of rubbery threads, which are arranged vertically at a spacing and along the horizontal direction generally over the range from the top to the bottom of the side jointing edges 21 and 22. The hip surrounding elastic member groups hold the paper diaper closely on the body by applying the horizontal shrinking forces to the hip surrounding portions at the front F and the back B. Here, the boundaries between the waist portion elastic members 24, 24, - - - , and so on and the hip surrounding elastic member groups 25, 25, - - - , and so on need not be completely clarified. Of the elastic members horizontally arranged and vertically spaced on the front F and the back B, for example, the elastic members on the upper side may function as the waist portion elastic members, although not the number is not specified, and the remaining elastic members may function as the hip surrounding elastic members.

In the back B, the back side curved elastic member groups 26, 26, - - - , and so on, as arranged separately of the hip surrounding elastic member groups 25, 25, - - - , and so on, are a plurality of, e.g., nine rubbery thread elastic members, which extend from the one-side jointing edge 22 generally along the leg surrounding cut line 29 to the crotch portion and which arrive, generally along the leg surrounding cut line 29 on the other side while passing over the crotch portion, at the side jointing edge 22 on the other side. These back side curved elastic member groups 26, 26, - - -, and so on are so arranged at a spacing as not to intersect each other. These back side curved elastic member groups 26, 26, - - -, and so on are different from the arrangement mode of the leg surrounding elastic members of the prior art. Specifically, two or three elastic extensible members are not so closely arranged as to form one bundle substantially, but five or more, preferably seven or more members are arranged at such a spacing as to form a predetermined stretchable zone.

The starting/trailing ends of the back side curved elastic member groups 26, 26, - - -, and so on are connected at predetermined spacings over the ranges from the upper portions to the lower portions of the jointing edges of the front F and the back B. At the portions to intersect the side edges of the absorbent body 10, also referred to as absorbent body side edges, the arrangement is made in the pattern, in which the intersection angle α on the acute angle side between the back side curved elastic member groups 26, 26, - - -, and so on and the side edges of the absorbent body 10 is 35 degrees or more, preferably 40 degrees or more; or more preferably 45 degrees or more. Incidentally in the shown example, the arrangement is made at the intersection angle α of about 47 degrees. This intersection angle α is desired to be 60 degrees at most, because of the balance between the horizontal component and the vertical component.

At the side jointing edges 21 and 22 between the front F and the back B, of the back side curved elastic member groups 26, 26, - - -, and so on, the elastic member $26_i$, as located at the position closest to the waist opening, is arranged such that the distance $S_B$ from the lowermost elastic member $24_o$ of the waist portion elastic members 24, 24, - - -, and so on is within 20 mm. When the wearer pulls up the sides of the waist portion, the pull of the paper diaper back B is facilitated by the elastic forces of the back side curved elastic member groups 26, 26, - - -, and so on thereby to improve the wearing easiness.

Moreover, it is desired that the back side curved elastic member groups 26, 26, - - -, and so on are directionally turned in an arcuately curve shape at the passing over portion of the crotch portion. In the elastic member, the shrinking force acts in the tangential direction but is turned at the crotch portion into the curved shape so that the force to act widthwise of the absorbent 13 can be minimized to prevent the absorbent 13 from shrinking at that crotch portion.

In this paper diaper 1, in order to fit the armoring sheet 20 at the back B to the bulging shape of the buttocks, the elastic member groups 26, 26, - - -, and so on are so arranged at the relatively gentle inclination angle that the shrinking force may act as much as possible along the bulge of the buttocks. If the elastic members 26, 26, - - -, and so on are arranged at the intersection angle of α=47 degrees, as shown, the shrinking force given can act up to 73% as a horizontal component so that the armoring sheet 20 can fit closely on the body while wrapping the buttocks. As a result, the absorbent body 10 can fit reliably on the body, without being shrunken toward the center side, thereby to enhance the leakage preventing effect.

Moreover, the arrangement spacing of the back side curved elastic member groups 26, 26, - - -, and so on at the side jointing edges 21 and 22 between the front F and the back B, that is, the arrangement spacing in an elastic member arrangement section BL of the side jointing edges 21 and 22 is substantially equalized to the arrangement spacing of the back side curved elastic member groups 26, 26, - - -, and so on in an elastic member arrangement section MB of the crotch portion. Of the back side curved elastic member groups 26, 26, - - -, and so on, the elastic member $26_o$, as located at the position closest to the crotch side, is arranged to draw such curves that the distance BH from the crotch portion folding line CL of the diaper is within ±50 mm, preferably within 35 mm. The arrangement spacings of the back side curved elastic member groups 26, 26, - - -, and so on are made equal at the side jointing edges 21 and 22 and the cloth portion so that the armoring sheet 20 can fit entirely in an even balance on the body without the elastic forces being concentrated. At the same time, the lines, as drawn by the back side curved elastic member groups 26, 26, - - -, and so on, are arranged to draw curves of large waves passing over the areas near the crotch portion, so that the armoring sheet 20 can be entirely held in close contact with the body. Incidentally, the method for arranging the back side curved elastic member groups 26, 26, - - -, and so on at equal spacings at the side jointing edges 21 and 22 and at the crotch portion is described in detail in connection with the later-described method for manufacturing the armoring sheet 20.

It is desired that the back side curved elastic member groups 26, 26, - - -, and so on, as arranged on the side of the back B, are offset at the crotch portion toward the front F with respect to the crotch portion folding line CL of the diaper. At the crotch portion, the back side curved elastic member groups 26, 26, - - -, and so on are biased toward the front F with respect to the crotch portion folding line CL of the diaper, so that the slid-down of the diaper, as might otherwise occur on the side of the buttocks, can be eliminated to fit the diaper on the body while eliminating the slack of the armoring sheet 20.

At the front of the armoring sheet 20, on the other hand, the abdomen side curved elastic member groups 28, 28, - - -, and so on, as arranged separately of the hip surrounding elastic member groups 25, 25, - - -, and so on, are also a plurality of or nine thread-shaped elastic members, in the shown example, which extend from the side jointing edge 21 on one side to the crotch side and reach the side jointing edge 22 on the other side while passing over the crotch, and which are arranged at a spacing but without intersection. These abdomen side curved elastic member groups 28, 28, - - -, and so on are arranged at a spacing but without intersection. These back side curved elastic member groups 26, 26, - - -, and so on are arranged differently of the leg surrounding elastic members of the prior art. In other words, two or three elastic members are not arranged at a close spacing substantially as a bundle, but five or more, preferably seven or more elastic members are so arranged at a predetermined spacing as to form a predetermined shrinking zone.

The starting/trailing ends of the abdomen side curved elastic member groups 28, 28, - - -, and so on are connected at predetermined spacings over the ranges from the upper portions to the lower portions of the side jointing edges 21 of the front F and the back B. At the portions to intersect the side edges of the absorbent body 10, the arrangement is made in the pattern, in which the intersection angle θ on the acute angle side between the abdomen side curved elastic member groups 28, 28, - - -, and so on and the side edges of the absorbent body 10 is 30 degrees or less, preferably 28 degrees or less. Incidentally in the shown example, the arrangement is made at the intersection angle θ of about 26 degrees. This intersection angle θ is desired to be 20 degrees or more at least, because of the balance between the horizontal component and the vertical component.

On these abdomen side curved elastic member groups 28, 28, - - -, and so on, too, in order to minimize the force to act in the widthwise direction of the absorbent 13 thereby to prevent the shrinkage of the absorbent 13 in that crotch portion, it is desired that the directions are turned generally in arcuate curves at the passing over portions of the crotch portion.

In this paper diaper 1, it is the tendency that the slip-down of the paper diaper prominently occurs mainly on the front F, because the body has no hanging bulge on the front unlike the back or the buttocks. In view of this knowledge, the elastic member groups 28, 28, - - -, and so on are arranged at a relatively sharp inclination angle. If the elastic members 28, 28, - - -, and so on are arranged at the intersection angle of θ=26 degrees, 90% or more of the given shrinking force can act as an upward component so that the paper diaper can be effectively prevented from slipping down.

At the side jointing edges 21 and 22 between the front F and the back B, of the abdomen side curved elastic member groups 28, 28, - - -, and so on, the elastic member $28_i$, as located at the position closest to the waist opening, is arranged such that the distance $S_F$ from the lowermost elastic member $24_o$ of the waist portion elastic members is within 20 mm. When the wearer pulls up the sides of the waist portion, the pull of the paper diaper front F is facilitated by the elastic forces of the abdomen side curved elastic member groups 28, 28, - - -, and so on thereby to improve the wearing easiness.

Moreover, the arrangement spacing of the abdomen side curved elastic member groups 28, 28, - - -, and so on at the side edges 21 and 22 between the front F and the back B, that is, the arrangement spacing in an elastic member arrangement section FL of the side jointing edges 21 and 22 is substantially equalized to the arrangement spacing of the abdomen side curved elastic member groups 28, 28, - - -, and so on in an elastic member arrangement section MF of the crotch portion. Of the abdomen side curved elastic member groups 28, 28, - - -, and so on, the elastic member 28o, as located at the position closest to the crotch side, is arranged to draw such curves that the distance FH from the crotch portion folding line CL of the diaper is within ±50 mm, preferably 35 mm. The arrangement spacings of the abdomen side curved elastic member groups 28, 28, - - -, and so on are made equal at the side jointing edges 21 and 22 and the cloth portion so that the armoring sheet 20 can fit entirely in an even balance on the body without the elastic forces being concentrated. At the same time, the lines, as drawn by the abdomen side curved elastic member groups 28, 28, - - -, and so on, are arranged to draw curves of large waves passing over the areas near the crotch portion, so that the armoring sheet 20 can be held in close contact with the body. Incidentally, the method for arranging the abdomen side curved elastic member groups 28, 28, - - -, and so on at equal spacings at the side jointing edges 21 and 22 and at the crotch portion is described in detail in connection with the later-described method for manufacturing the armoring sheet 20.

Here, it is desired that the elastic member $28_o$, as located at the position closest to the crotch side, of the abdomen side curved elastic member groups 28, 28, - - -, and so on arranged on the front side F, and the elastic member $26_o$, as located at the position closest to the crotch side, of the back side curved elastic member groups 26, 26, - - -, and so on arranged on the back side B are close to each other in the crotch portion but without any intersection. It is desired that the closest width (FH–BH) is 10 to 20 mm. At the crotch portion, the absorbent body 10 is pushed to contact with the body sides under equivalent pressures by the curved elastic member groups 28 - - -, and 26 - - -, so that the clearances from the body is sealed to exhibit a high leakage preventing effect.

Figure 6:
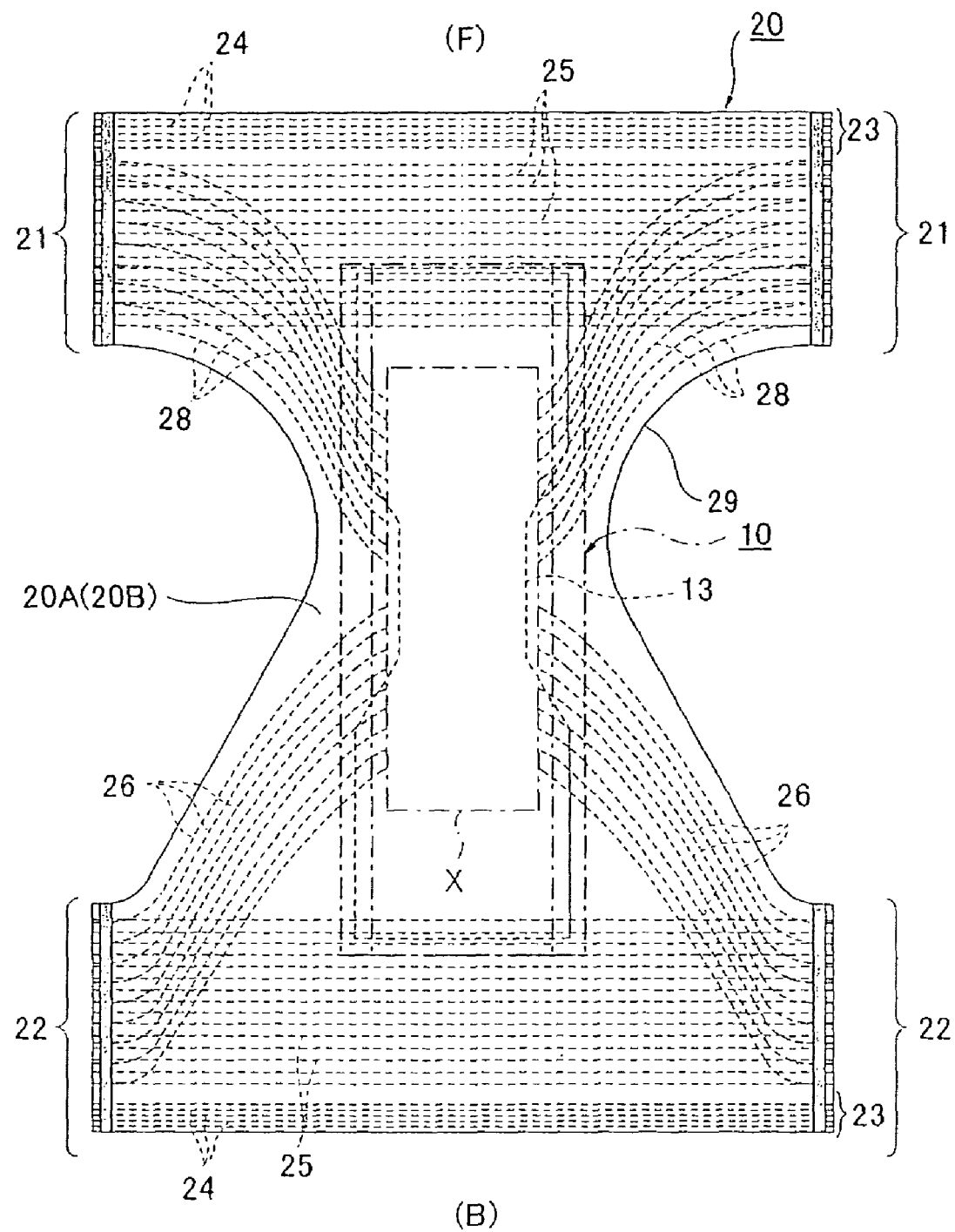
FIG. 6 is a developed diagram showing a modification of the armoring sheet 20.

Here in the embodiment thus far described, the hip surrounding elastic member groups 25, 25, - - -, and so on, and the curved elastic members 26 - - -, and 28 - - -, as arranged at the front F and the back B, are continuously arranged on the absorbent body 10, too. As shown in FIG. 6, however, the elastic members across the absorbent body 10 may be cut and discontinuously arranged. The absorbent 13 can be more prevented from shrinking by making the elastic members discontinuous on the absorbent body. In case the curved elastic member groups 26 - - - and 28 - - - are cut and discontinued on the absorbent 13 (but not the absorbent body), they may be cut at the line positions in the longitudinal direction, as shown in FIG. 6, or the curved elastic member groups 26 - - - and 28 - - - may be cut at the positions substantially along the side edge shape lines of the absorbent 13, i.e., along the wrapping shape. In case the cut positions of the curved elastic members are changed according to the side edge shapes of the absorbent, the absorbent 13 can be held in contact with the body by keeping the tensions of the elastic members 26 - - - and 28 - - - effectively while preventing the shrinkage of the absorbent.

Here, so long as the hip surrounding elastic member groups 25, 25, - - -, and so on and the curved elastic members 26 - - - and 28 - - - are arranged in the states before cut, in accordance with the invention whether or not the elastic members might be cut on the absorbent body 10, these arrangements should be contained in the generic scope of the invention.

(Method for Fixing the Elastic Members 24 to 28, and Method for Manufacturing the Armoring Sheet 20)

Next, the method for manufacturing the armoring sheet 20 is described in detail.

Figure 7:
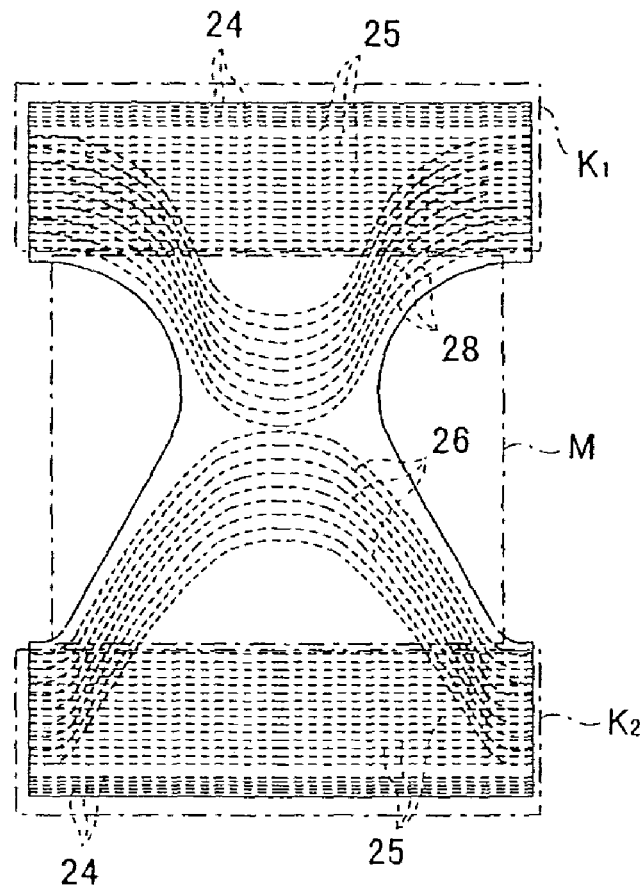
FIG. 7 is a diagram dividing the application direction of elastic members in the armoring sheet.

In this armoring sheet 20, as shown in FIG. 7, in hip surrounding shearing zones $K_1$ and $K_2$, the waist portion elastic members 24, 24, - - -, and so on and the hip surrounding elastic member groups 25, 25, - - -, and so on are fixed on the armoring sheet 20 by the adhesive applied to the circumferences of the waist portion elastic members 24, 24, - - -, and so on and the elastic members 25, 25, - - -, and so on. The curved elastic member groups 26 - - -, and 28 - - - are fixed not by applying an adhesive to their peripheries but by using the adhesive applied to the peripheries of the hip surrounding elastic members 25, 25, - - -, and so on at the intersecting portions with the hip surrounding elastic members 25, 25, - - -, and so on. In the diaper intermediate zone M other than the hip surrounding shearing zones $K_1$ and $K_2$, on the other hand, the curved elastic member groups 26 - - - -, and 28 - - - are fixed by the adhesive which is applied to the nonwoven fabric 20A (20B) on at least one side of the armoring sheet 20.

Figure 8:
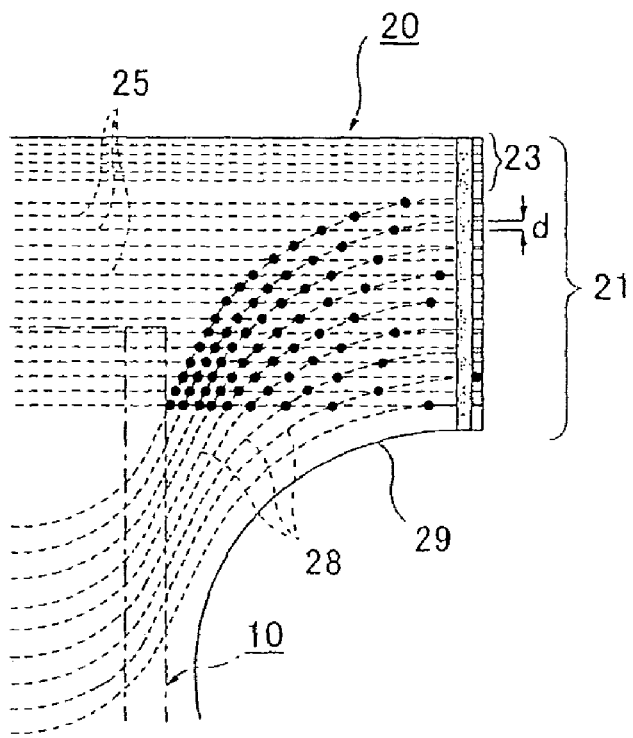
FIG. 8 is an explanation diagram of the fixing mode of curved elastic extensible members 28 at the side portions of the armoring sheet 20.

In the hip surrounding shearing zones $K_1$ and $K_2$, specifically, the hip surrounding elastic members 25, 25, - - - and so on are fixed, after the hot-melt adhesive was applied to the peripheries of the elastic members 25, according to the well-known control seam method, and then by introducing them into the armoring sheet 20. However, the back side curved elastic member groups 26, 26, - - -, and so on and the abdomen side curved elastic member groups 28, 28, - - -, and so on are fixed, without applying the adhesive to their peripheries, but when introduced into the armoring sheet 20, together with the hip surrounding elastic members 25, 25, - - -, and so on by the hot-melt adhesive applied to the peripheries of the hip surrounding elastic members 25, 25, - - -, and so on at the intersecting portions of the hip surrounding elastic members 25, 25, - - -, and so on. As a result, at the side portions, as shown in FIG. 8 (showing the side portion of the abdomen side), the abdomen side elastic members 28, 28, - - -, and so on are fixed, only at the intersecting portions (as indicated by symbols ●) with the hip surrounding elastic members 25, on the hip surrounding elastic members 25 (and on the armoring sheet 20, too, by the extension of the adhesive). At the side portions where the elastic members 25 - - - , 26 - - - and 28 - - - are crowded, therefore, the amount and range of the adhesive to be used can be minimized so that the sheet can be prevented from being hardened by the adhesive and can be given softness.

In this case, at the two side portions where the front F and the back B of the armoring sheet are jointed, the spacing distances d between the hip surrounding elastic members 25, 25, - - - , and so on and the curved elastic members 26 - - - , and 28 - - - are desired to be 1 mm or less. At the side portions, more specifically, the intersections between the hip surrounding elastic members 25, 25, - - - , and so on and the curved elastic members 26 - - - , and 28 - - - are brought closer to the side edge portions so that the retractions of the curved elastic members 26 - - - , and 28 - - - can be eliminated, when cut at the two side edge corresponding positions in the paper diaper manufacturing process, to bring the starting/trailing ends of the curved elastic members 26 - - - , and 28 - - - closer to the side edges.

Figure 11:
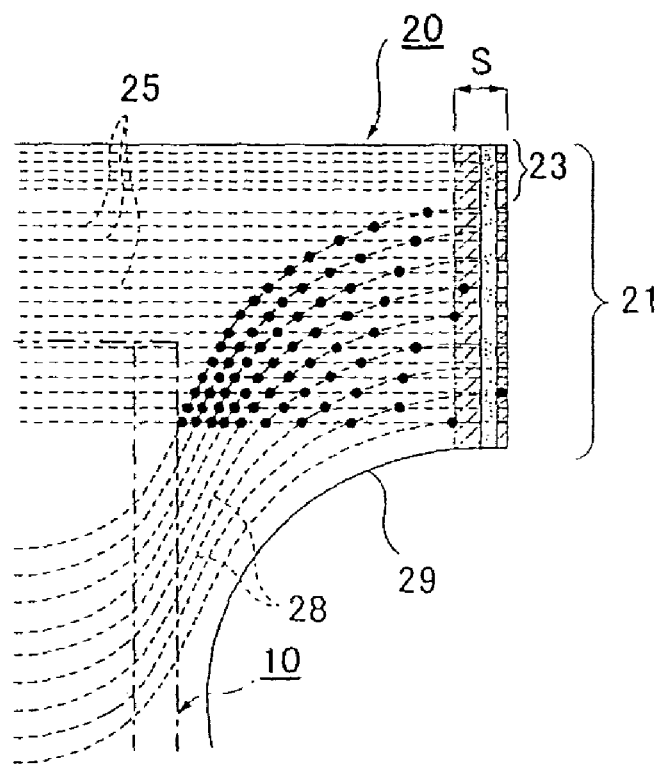
FIG. 11 is an explanatory diagram of a fixing mode (a modification) of the curved elastic members 28 at the side portion of the armoring sheet 20.

Here, in order to completely eliminate the retractions of the curved elastic members 26 - - - , and 28 - - - at the cutting time, at the two side portions, to which the front F and the back B of the armoring sheet 20 are jointed, as shown in FIG. 11, the hot-melt adhesive may be applied in an auxiliary manner to the range S of 5 to 20 mm inward from the side edge portions of the armoring sheet 20, thereby to fix the curved elastic member groups 26 - - - , and 28 - - - to the armoring sheet 20 by the hot-melt adhesive. In this case, as shown in FIG. 9(B), a curtain application may be performed so partially (at a P area) across the diaper cutting portion (as indicated by chain lines) of the hip surrounding shearing zones.

In the intermediate zone M other than the hip surrounding shearing zones, on the other hand, the hot-melt adhesive is applied to the nonwoven fabric 20A (20B) of at least one side of the armoring sheet 20, and the curved elastic members 26 - - - , and 28 - - - are then introduced and fixed to the adhesive applied faces.

Figure 9:
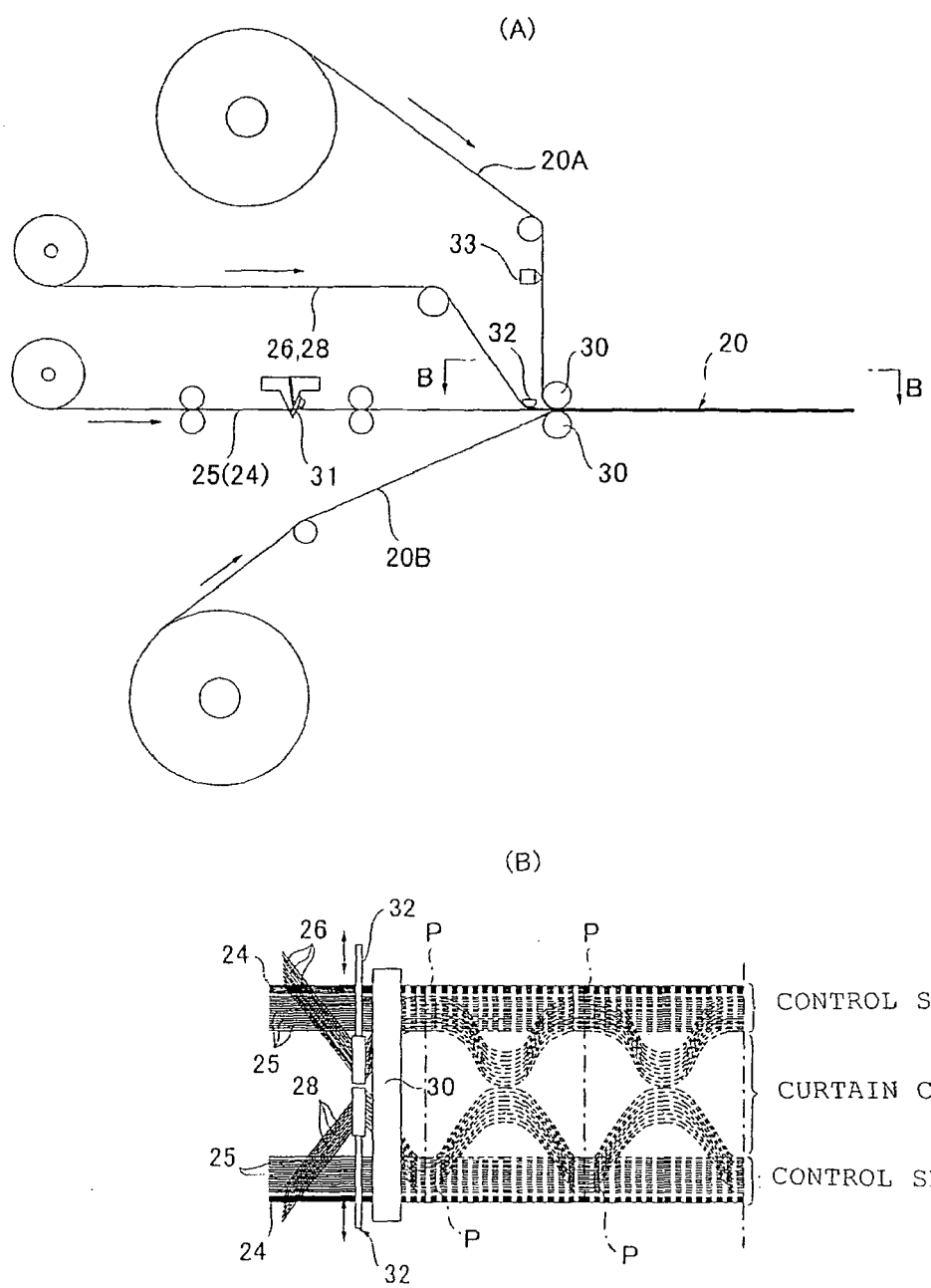
FIG. 9 shows an assembling procedure of the armoring 20, and (A) presents a schematic diagram, and (B) presents a top plan view of an essential portion.

When the armoring sheet 20 is to be manufactured, as shown in FIG. 9, the upper-layer nonwoven fabric 20A is fed to the upper side of the nip roller unit 30, and the lower-layer nonwoven fabric 20B is fed to the lower side. Various elastic members (e.g., the waist portion elastic members 24, the hip surrounding elastic members 25, the back side curved elastic members 26 and the abdomen side curved elastic members 28) are fed to between those upper-layer nonwoven fabric 20A and the lower-layer nonwoven fabric 20B. At the step of assembling the armoring sheet 20, the hot-melt adhesive is applied to the peripheries of the waist portion elastic members 24 and the hip surrounding elastic members 25 by a periphery applying device 31, and these members are fed to a nip roller unit 30.

Figure 10:
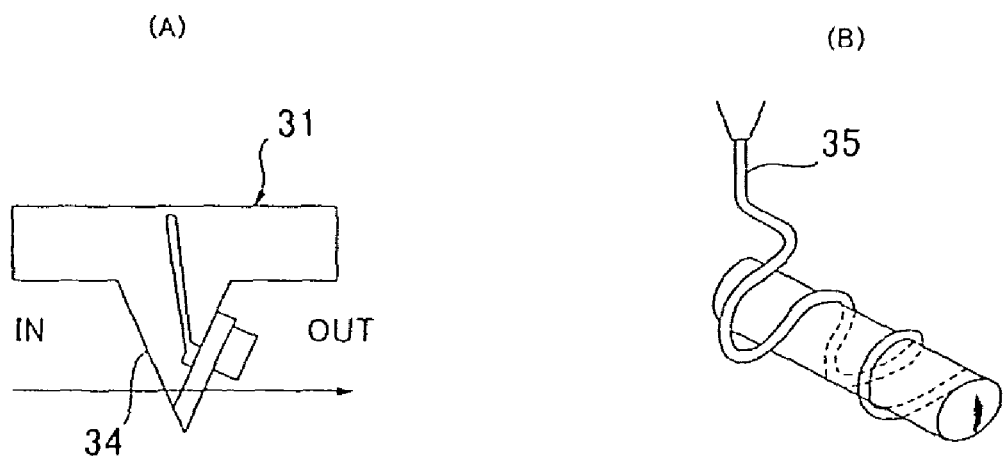
FIG. 10 presents diagrams showing an adhesive application example in a control seam method.

The periphery applications of the elastic members 24 - - - , and 25 - - - are performed by the application method using the comb gun 31, which guides the elastic members while feeding the adhesive to the bottom of a V-shaped groove by using a member 34 having the groove, as shown in FIG. 10(A), the omega ($\Omega$) member using application method for applying the adhesive to the elastic members by using the omega-shaped ring member, or the well-known control seam application method for applying the adhesive while entangling and passing the elastic members on a bent member 35, as shown in FIG. 10(B).

On the other hand, the aforementioned curved elastic members 26 - - - , and 28 - - - are introduced, while being meandered by the well-known traverse device 32, into the nip roller unit 30. This traverse device 32 has holding portions for the elastic members 26 - - - , and 28 - - - at the leading end portions, and moves the elastic members back and forth at a calculated speed widthwise of the continuous web (i.e., the upper and lower nonwoven fabric sheets 20A and 20B), thereby to arrange the elastic members 26 - - - , and 28 - - - in a predetermined curved shape. As a result, the arrangement spacing of the curved elastic members 26 and 28 can be automatically made equivalent at the side jointing edges 21 and 22 and at the crotch portion. In the invention, the elastic members are introduced without the hot-melt adhesive being applied to the peripheries thereof, so that the hip surrounding shearing zones are fixed at the intersections with the hip surrounding elastic members 25, 25, - - - , and so on, by the adhesive applied to the peripheries of the hip surrounding elastic members 25, 25, - - - , and so on.

On the other hand, the hot-melt adhesive is curtain-applied by the coater 33 to at least one side of the upper-layer nonwoven fabric 20A and the lower-layer nonwoven fabric 20B, that is, in the shown embodiment, to the area corresponding to the diaper intermediate zone M of the upper-layer nonwoven fabric 20A other than the hip surrounding shearing zones. The curved elastic members 26 - - - , and 28 - - - are fixed at the diaper intermediate zone M by the hot-melt adhesive applied to the upper-layer nonwoven fabric 20A.

Here, the hot-melt adhesive is exemplified by an EVA family, an adhesive rubber family (or an elastomer family), an olefin family or a polyester/polyamide family. In this disposable diaper, it is desired to use the adhesive rubber family (or the elastomer family).

Here in the case of the method, in which the hot-melt adhesive is homogeneously applied in the curtain shape to the sheet side elastic member arrangement areas in the diaper intermediate zone M other than the hip surrounding shearing zones and in which the elastic members are introduced and fixed on the areas, the sheet itself may become hard to deteriorate the wearing feeling. In recent years, therefore, there has been proposed a method (as will be called the "bead application method"), in which the elastic members are fixed by applying the adhesive in a plurality of rows at a predetermined spacing.

Figure 18:
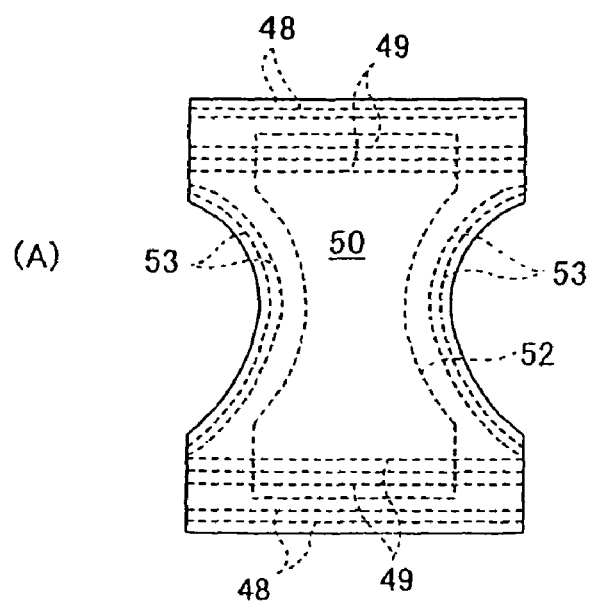
FIG. 18 presents a pants type disposable paper diaper (No. 1) of the prior art, and (A) presents a developed diagram, and (B) is a product state diagram.
Figure 18:
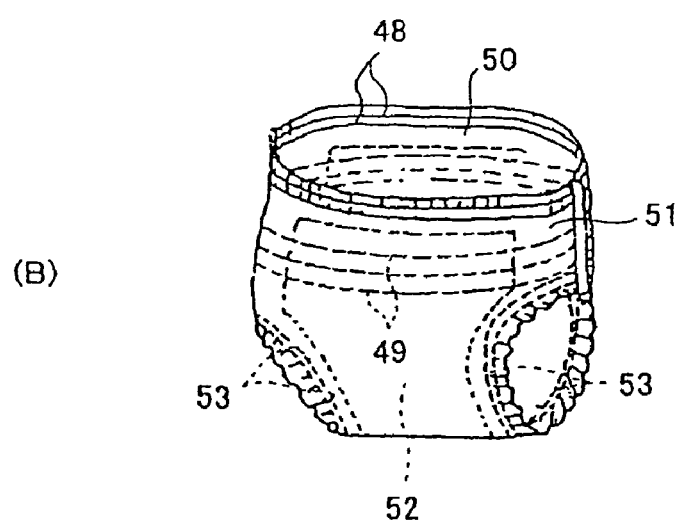
Figure 19:
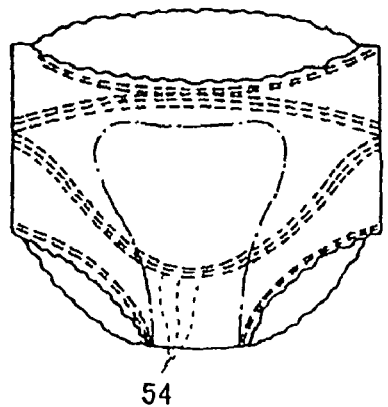
FIG. 19 is a front elevation showing a pants type disposable paper diaper (No. 2) of the prior art.
Figure 20:
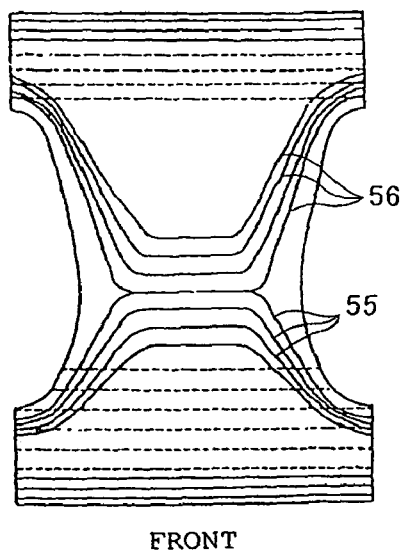
FIG. 20 is a developed diagram showing a pants type disposable paper diaper (No. 3) of the prior art.
Figure 21:
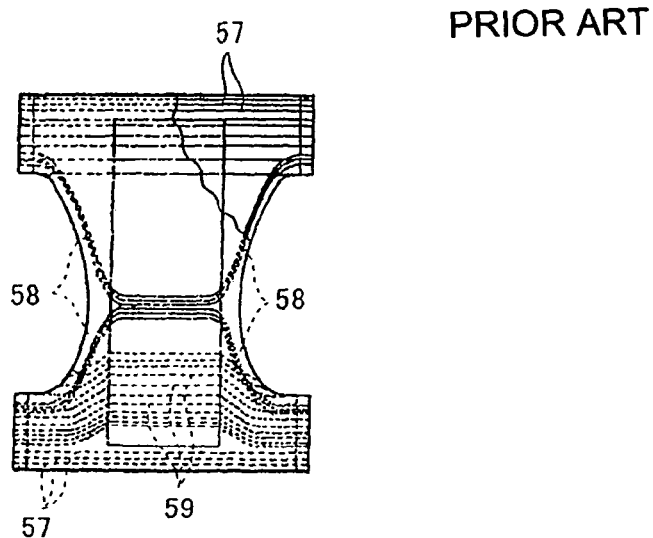
FIG. 21 is a developed diagram showing a pants type disposable paper diaper (No. 4) of the prior art.
Figure 22:
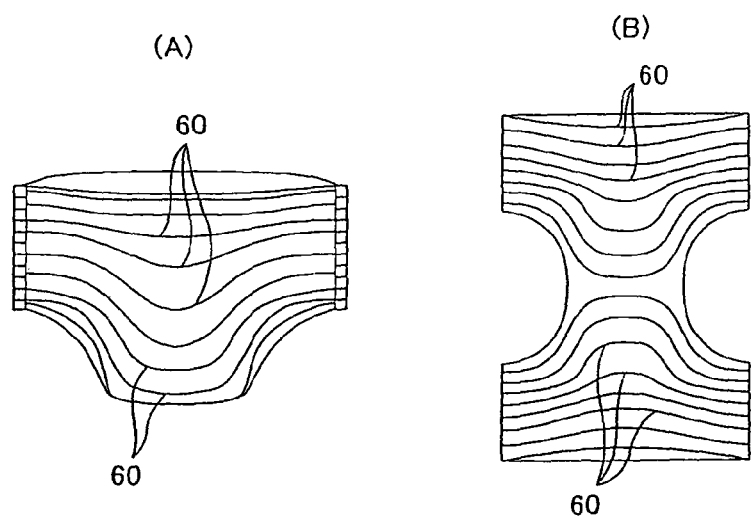
FIG. 22 presents a pants type disposable paper diaper (No. 5) of the prior art, and (A) presents a front elevation, and (B) is a developed diagram.

As shown in FIG. 18, however, under the condition of adopting the bead application method, when the elastic members are cut on the absorbent so as to eliminate the shrinkage of the absorbent, there arises a problem that the fixing points (or the fixing point line L) of the elastic members become irregular and zigzag. This problem raises resultant problems that the absorbent is deteriorated in fitness or wrinkled, and that the appearance is degraded.

The following method can be properly adopted to cut and discontinue the elastic members crossing the absorbent body 10, while solving the aforementioned problems.

Figure 12:
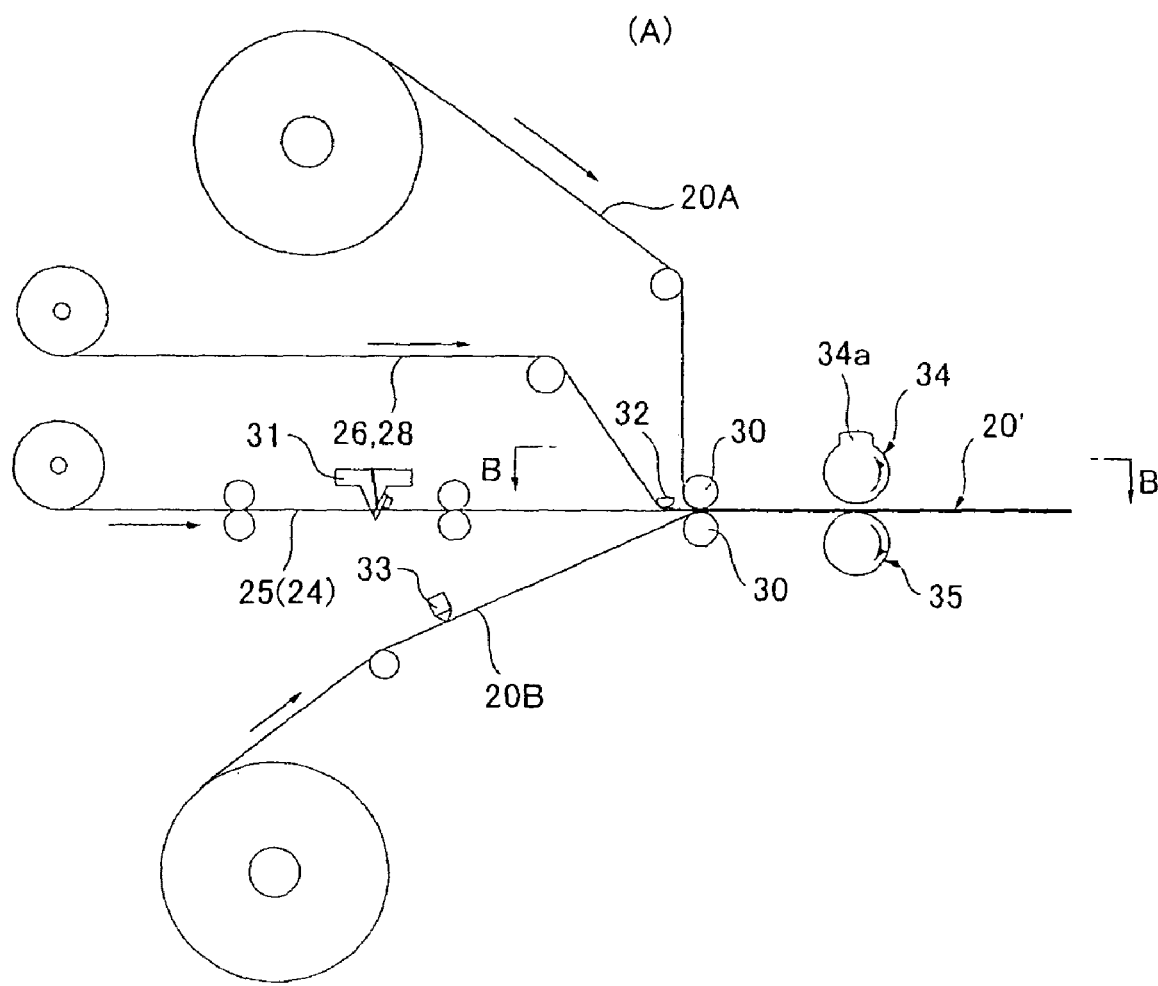
FIG. 12 shows the assembling procedure of the armoring 20 in case the curved elastic members are cut on the absorbent, and (A) presents a schematic diagram, and (B) presents a top plan view of an essential portion.
Figure 12:
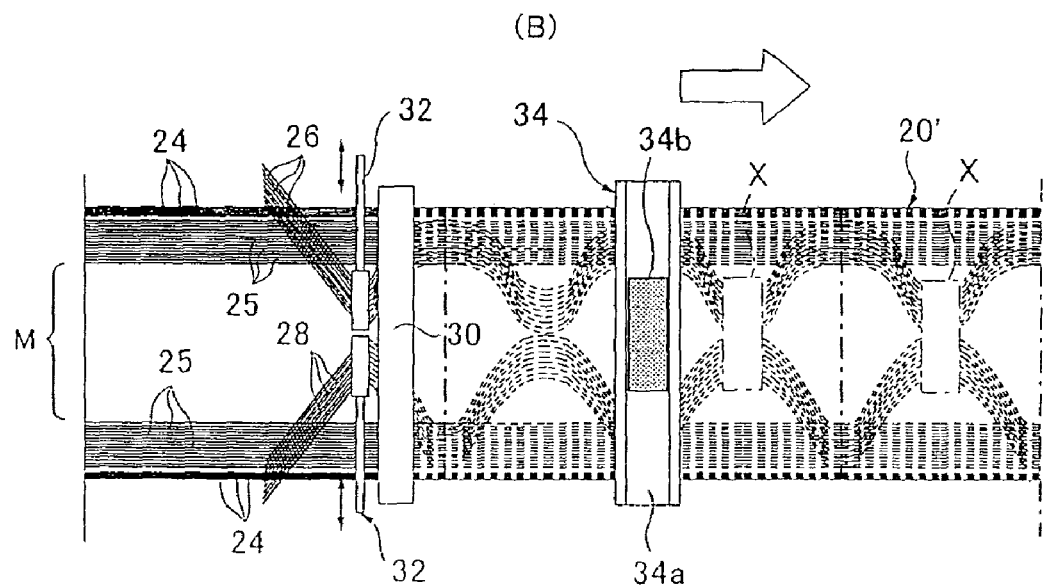

For manufacturing the armoring sheet 20, as shown in FIG. 12, the upper-layer nonwoven fabric 20A is fed to the upper side of the nip roller unit 30, and the lower-layer nonwoven fabric 20B is fed to the lower side. Various elastic members (e.g., the waist portion elastic members 24, the hip surrounding elastic members 25, the back side curved elastic members 26 and the abdomen side curved elastic members 28) are fed to between those upper-layer nonwoven fabric 20A and the lower-layer nonwoven fabric 20B so that the armoring sheet 20 is continuously assembled.

The waist portion elastic members 24 and the hip surrounding elastic members 25 are fixed to the sheet by applying the hot-melt adhesive to the peripheries of the elastic members 24 - - - , and 25 - - - by the periphery applying device 31 and by feeding them to the nip roller unit 30.

For the intermediate zone M between the hip surrounding elastic member 25, 25, - - -, and so on of the front and the hip surrounding elastic member 25, 25, - - -, and so on of the back, on the other hand, one of the upper-layer nonwoven fabric 20A and the lower-layer nonwoven fabric 20B, i.e., the lower-side nonwoven fabric 20B of the shown example is so bead-applied by a coater 33 as to form a plurality of rows at a vertical spacing in the horizontal direction, so that the curved elastic members 26 - - - -, and 28 - - - are fixed on the aforementioned intermediate zone M by the hot-melt adhesive applied to the lower-layer nonwoven fabric 20B.

For cutting and discontinuing the curved elastic members 26 - - -, and 28 - - - on the absorbent body 10, there is properly adopted the cutting method, which is described in JP-A-2002-35029, JP-A-2002-178428 and JP-A-2002-273808. In the elastic member cutting method described in those JP-A, basically as shown in FIG. 12, after a laminated sheet 20' to become the armoring sheet 20 was prepared, the laminated sheet 20' is passed between the emboss heat roll 34 having a plurality of kicks arrayed on its surface and the confronting roll 35 confronting the emboss heat roll 34, so that the curved elastic members 26 - - -, and 28 - - - of that laminated sheet 20' are pressed or heated and are cut between the kicks of the emboss heat roll 34 and the confronting roll 35. Here, the X area in FIG. 6 and FIG. 12(B) indicates the cut range.

Figure 13:
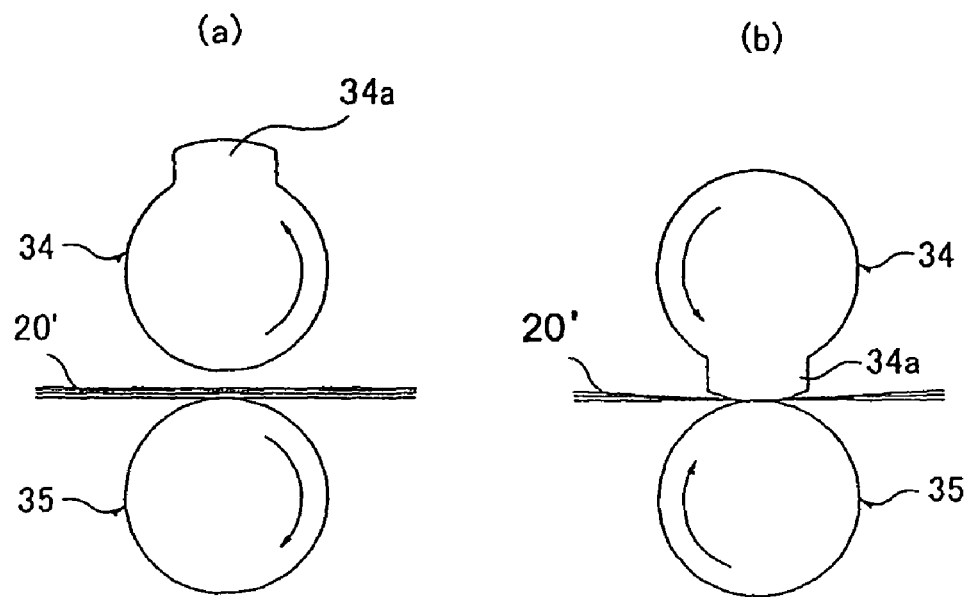
FIG. 13 presents explanatory views of the operation mode of an emboss heat roll and a confronting roll.

The confronting roll 35 may be spaced from the emboss heat roll 34, as shown in FIG. 13(a), so that it may abut against only the emboss portion 34a of the emboss heat roll 34. As these two rolls rotate, as shown in FIG. 13(B), the emboss portion 34a is moved downward to come into abutment against the confronting roll 35. On the emboss portion 34a, small kicks 40 to 43 are further formed substantially in an hourglass shape on a defining area 34b, as shown in FIG. 14. As a matter of fact, those kicks 40 to 43 abut against the confronting roll 35 at the tip faces thereof.

Figure 14A:
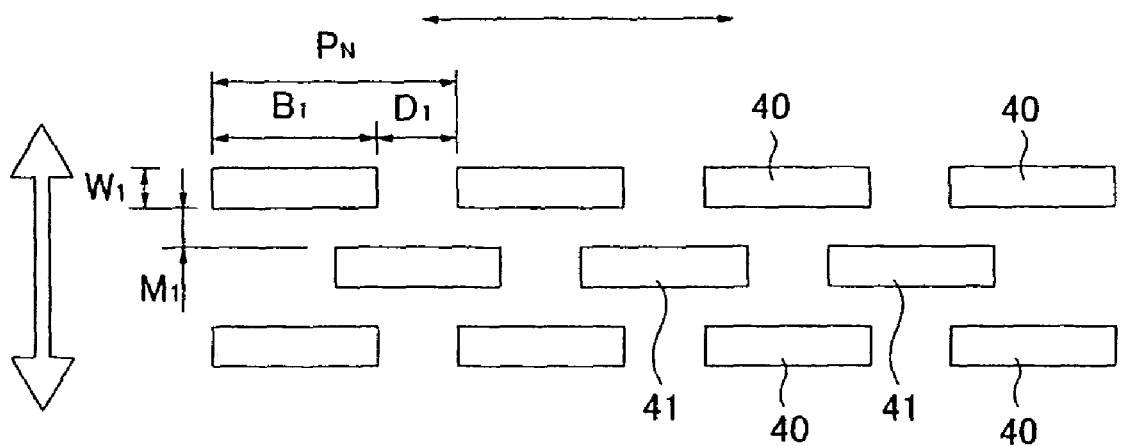
FIGS. 14(a) and 14(b) are explanatory views showing examples of emboss patterns of a staggered array.
Figure 14B:
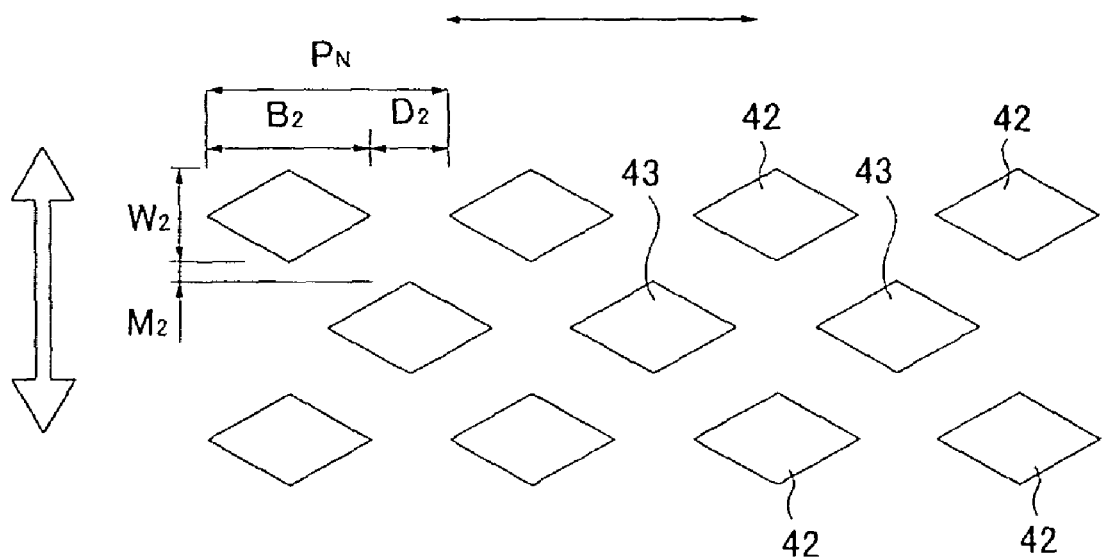

The preferred examples of the emboss pattern are shown in FIGS. 14(a) and 14(b). FIG. 14(a) shows the emboss pattern, in which a plurality of linear kicks are arranged in a staggered shape. This emboss pattern is constituted by alternately repeating rows of kick groups, in which the linear kicks 40 having a length $S_1$ and a width W1 are arrayed at a distance D1 in the axial direction (of the black arrows) of the emboss heat roll 34, and rows of kick groups, in which the kicks 41 and 41 having the same length B1 and the width W1 as those of the kicks 40 are so arrayed in the circumferential direction (of the blank arrows) of the emboss heat roll 34 and at a spacing of M1 from the kicks 40 that the longitudinal center line of the kicks 41 may pass through the points of 2/D1. FIG. 14(b) shows the pattern, in which rhombic kicks are arranged in a staggered shape. This emboss pattern is constituted by alternately repeating rows of kick groups, in which the rhombic kicks 42 and 42 having a longer axis B2 and a shorter axis W2 are arrayed at a distance D2 in the axial direction (of the black arrows) of the emboss heat roll 34, and rows of kick groups, in which the kicks 43 and 43 having the same rhombic shape as that of the kicks 42 are so arrayed in the circumferential direction (of the blank arrows) of the emboss heat roll 34 and at a spacing of M2 from the kicks 42 that the shorter axis of the kicks 42 may correspond to the point of 2/D2.

The length B1 of the linear kicks and the longer axis B2 of the rhombus is preferably within a range of 1 to 25 mm, and more preferably within a range of 5 to 25 mm. Moreover, the spacing distance D1 from the adjoining kick is preferably equal to or shorter than B1. Because of the staggered arrangement, an elastic member positioned between the kick 40 and the kick 40, can be reliably cut at the kick 41. The relation between D2 and B2 is preferably at D2≦B2. If B1 or B2 is smaller than 1 mm, the elastic members may not be able to be cut, as the case may be. If the length is more than 25 mm, the seal portion may have such a larger area as to deteriorate the touch feeling. Therefore, the ranges of D1 and D2 are preferably within 1 to 25 mm, and the range of D1 is more preferably within 3 to 25 mm. In case the kicks are rhombic, the corner portions of the kicks adjoining in the roll circumferential direction may overlap slightly, as viewed in the elastic member attaching direction. Then, the elastic members may be unable to be cut escaping the seal portion. Therefore, the range of D2 is more preferably 3 to 10 mm.

The width W1 of the linear kicks and the shorter axis W2 of the rhombus are preferably 0.5 to 15 mm. The elastic members cannot be cut, if less than 0.5 mm, and the area of the seal portion is excessively large, if more than 15 mm, thereby to deteriorate the touch feeling. It is more referable that the lower limit of W2 is 1 mm or more.

The distance between the rows of the kick groups is preferred to have the M1 or M2 of 5 to 25 mm, although not especially limited. The shape of the kicks should not be limited to the aforementioned linear or rhombic shape but can be oblique lines, circles, triangles, stars or other polygons. The kicks can also be changed at every rows.

Figure 15:
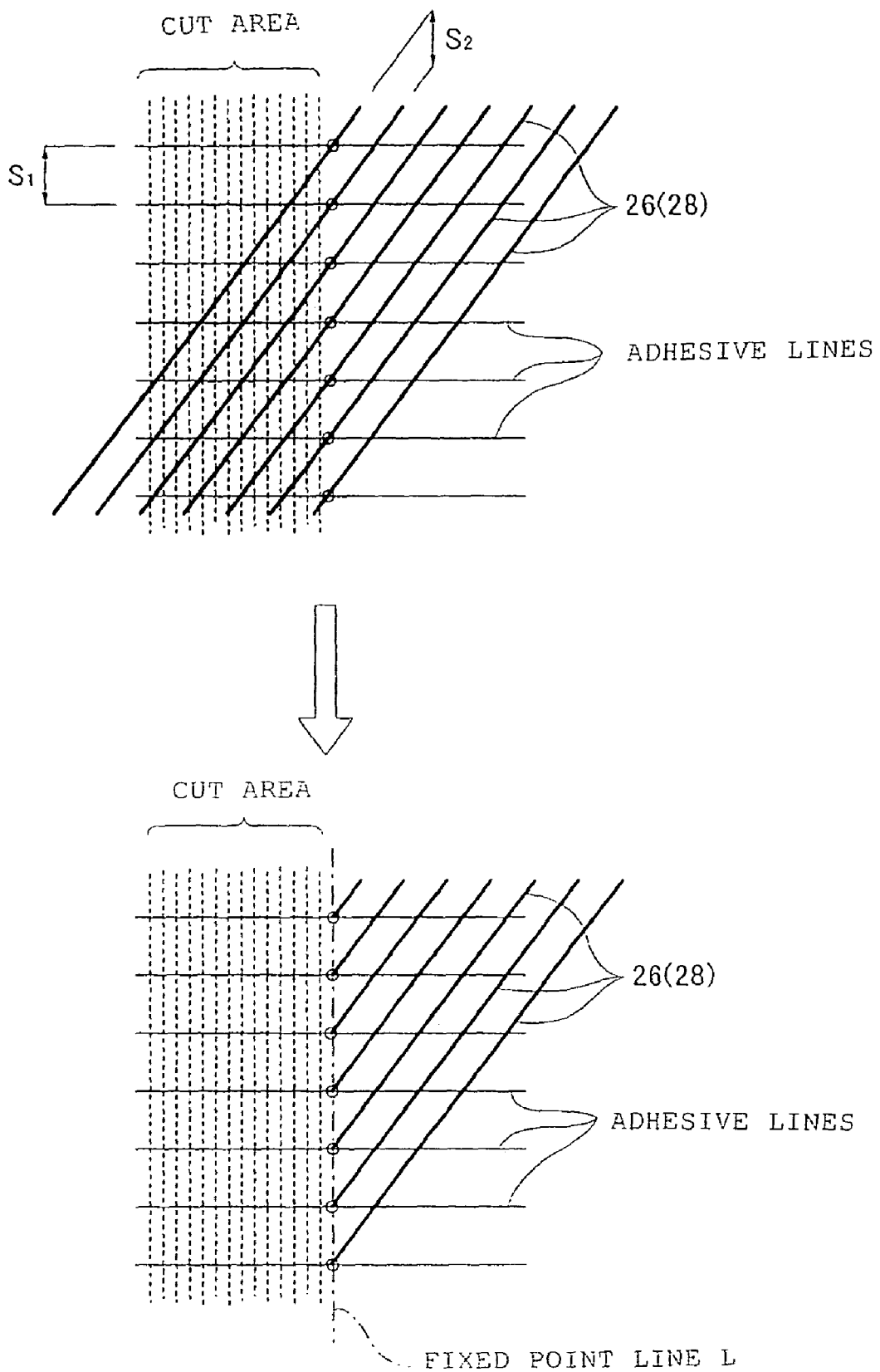
FIG. 15 presents explanatory views showing a method according to the invention for cutting curved elastic members 26 - - - , and 28 - - - .

In the disposable diaper, when the curved elastic members 26 - - -, and 28 - - - are cut and discontinued on the absorbent body 10, the fixing points of the individual curved elastic members 26 - - - -, and 28 - - - are arrayed generally on a common line in the longitudinal direction of the diaper. For this array, as shown in FIG. 15, the ratio between the spacing width $S_1$ of the adhesive and the spacing width $S_2$ in the direction of the adhesive spacing width between the curved elastic members 26 - - -, and 28 - - - is set substantially to an integral multiple, e.g., one time in the shown embodiment. Then, the intersections (as indicated by symbols ○) between the adhesive lines and the curved elastic members 26 - - -, and 28 - - - are regulated to predetermined positions in the longitudinal direction of the diaper. If the curved elastic member groups 26 - - - -, and 28 - - - are cut on the absorbent body 10 at the line positions along the longitudinal direction of the diaper, the fixed points of the curved elastic members 26 - - -, and 28 - - - are arranged generally on the common linear line (or the fixed point line L) in the diaper longitudinal direction.

Figure 16A:
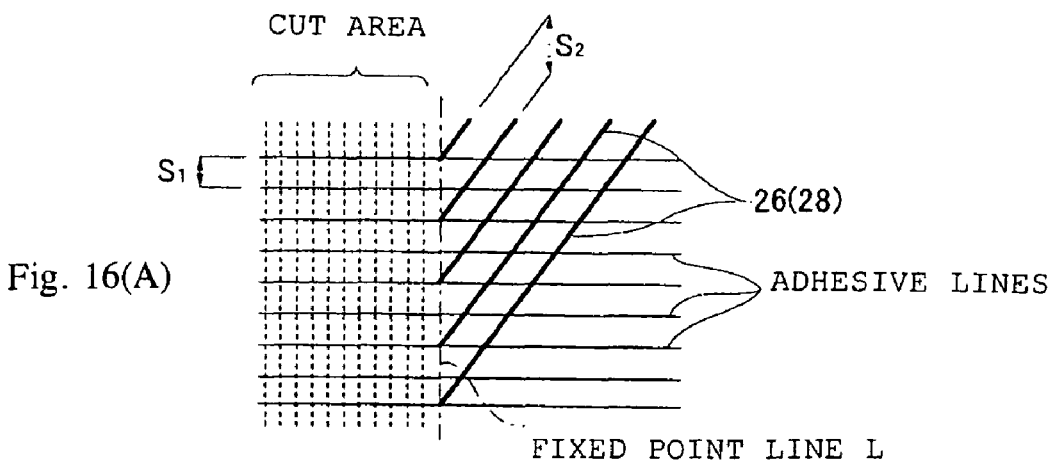
FIGS. 16(A) to 16(C) are diagrams showing modifications of the cutting method of the invention.
Figure 16B:
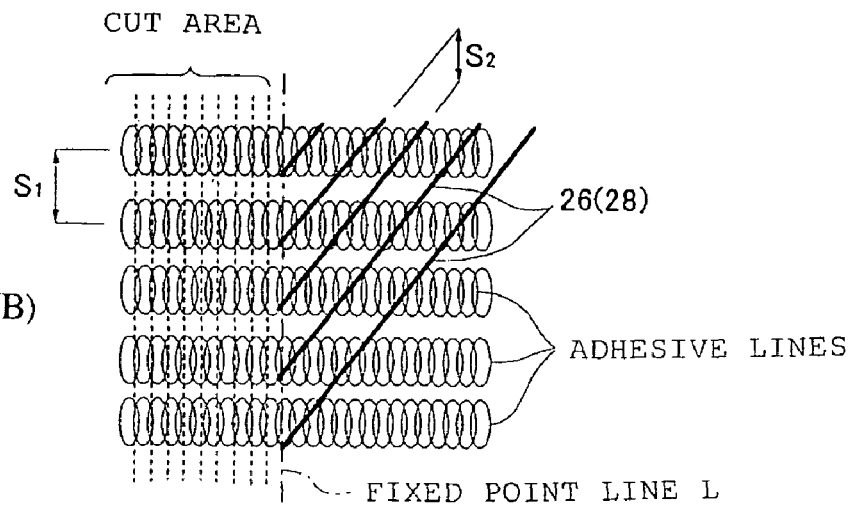
Figure 16C:
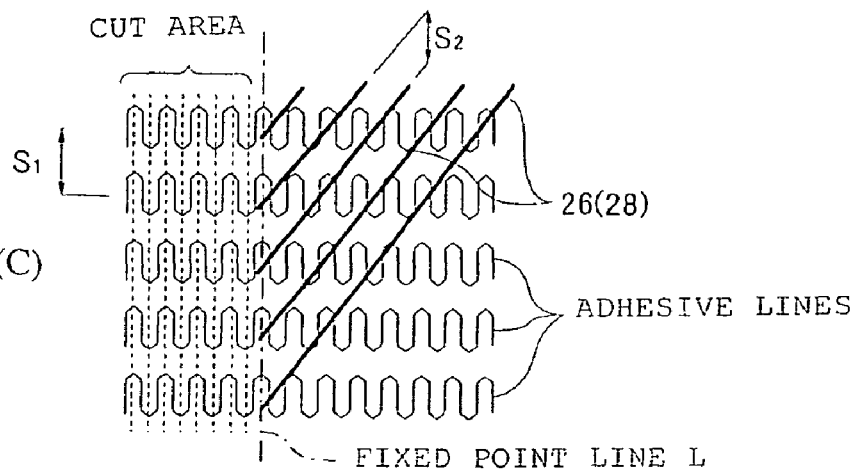
Figure 17:
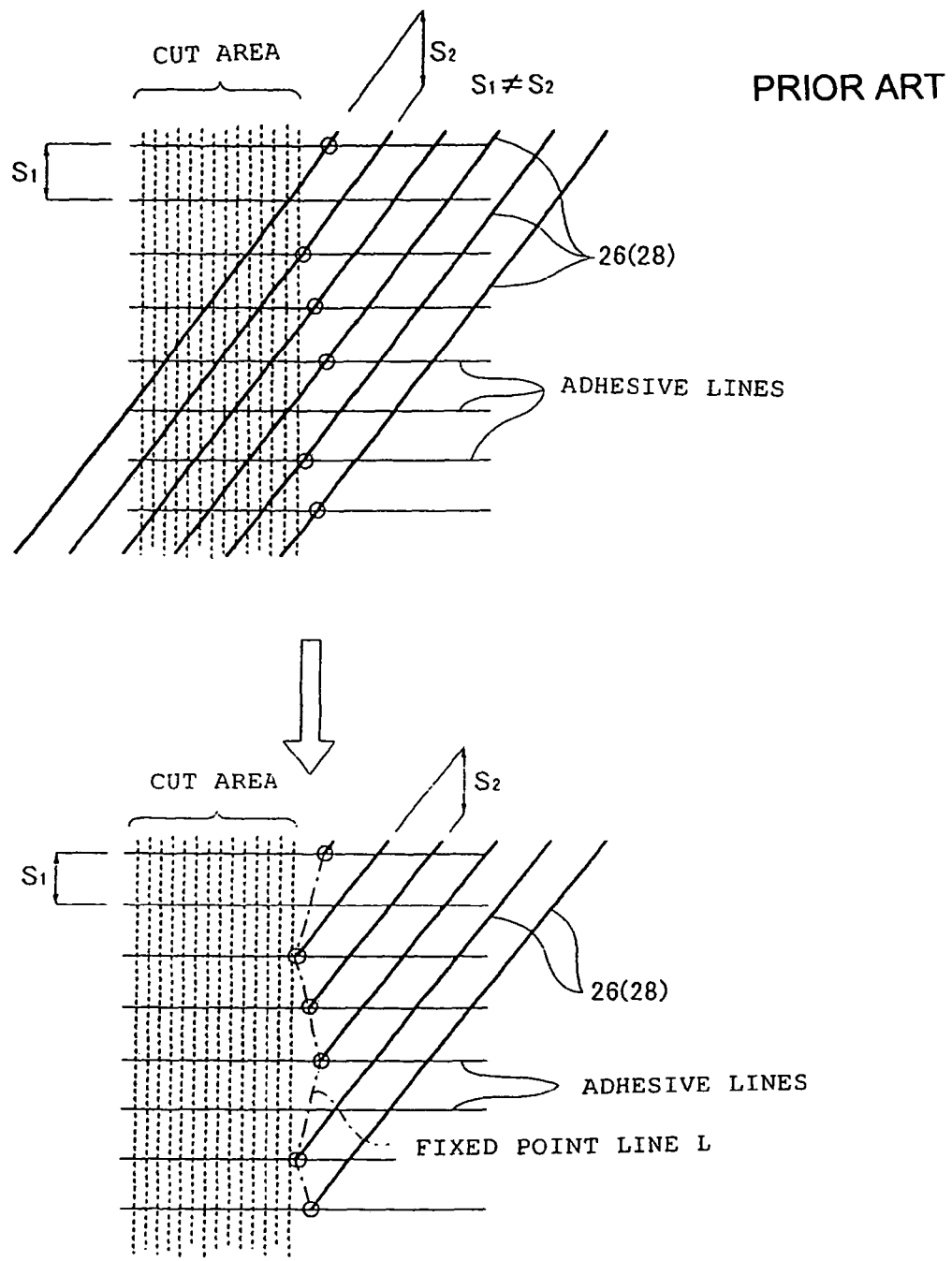
FIG. 17 presents diagrams for explaining the problems in the curved elastic member cutting method of the prior art.

Some embodiments are presented in the following. For example, FIG. 16(A) shows an embodiment, in which the ratio between the spacing width $S_1$ of the adhesive and the spacing width $S_2$ between the curved elastic members 26 - - - -, and 28 - - - in the width direction of the adhesive spacing is set to about two times. Moreover, the adhesive lines should not be limited to linear beads, but may be modified, as shown in FIG. 16(B), such that the individual adhesive lines are spirally applied to form a plurality of rows as a whole, and, as shown in FIG. 16(C), such that the individual adhesive lines are applied in undulating shapes by the summit spray to form a plurality of rows as a whole.

(Assembly of Paper Diaper)

The absorbent body 10 and the armoring sheet 20 are integrated, as shown in FIG. 2, such that the absorbent body 10 is adhered to and integrated with the upper face side of the armoring sheet 20 by the adhesive such as the hot melt. Then, the absorbent body 10 and the armoring sheet 20 are longitudinally folded, and their two side portions are thermally welded or jointed to each other by the hot-melt adhesive so that the pants-type paper diaper is assembled.

Another Embodiment (1) In the foregoing embodiment, the lowermost crotch side elastic member $28_o$ of the abdomen side curved elastic member groups 28, 28, - - -, and so on, as arranged on the front F, and the lowermost crotch side elastic member $26_o$ of the back side curved elastic member groups 26, 26, - - -, and so on, as arranged on the back B, are so disposed close to each other as to have no intersection in the crotch portion. However, the abdomen side curved elastic member groups 28, 28, - - -, and so on and the back side curved elastic member groups 26, 26, - - - and so on may partially intersect with each other.

DESCRIPTION OF REFERENCE NUMERALS AND SIGNS

1 - - - Paper Diaper, 10 - - - Absorbent Body, 11 - - - Liquid-Permeable Surface Sheet, 12 - - - Leakage-Proof Sheet, 13 - - - Absorbent, 14 - - - Crepe Paper, 15 - - - Gathered Nonwoven Fabric, 16 - - - Filament Elastic Extensible Member, 20 - - - Armoring Sheet, 21, 22 - - - Side Jointing Edge, 24 - - - Waist Portion Elastic Members, 25 - - - Hip Surrounding Elastic Member, 26 - - - Back Side Curved Elastic Member, 28 - - - Abdomen Side Curved Elastic Member, 29 - - - Leg Surrounding Cut Line, F - - - Front, and B - - - Back.

The invention claimed is:

1. A pants type disposable diaper comprising:
an absorbent body including an absorbent, said absorbent body having an outer face side, front and back ends, and absorbent body side edges extending between said front and back ends with a longitudinal direction of said diaper extending between the front end and the back end;
an armoring sheet disposed fixed to the outer face side of said absorbent body;
said armoring sheet including:
a front portion having left and right front side jointing edges extending in the longitudinal direction and having a front top portion forming a front waist portion;
a back portion having left and right back side jointing edges extending in the longitudinal direction and having a back top portion forming a back waist portion; and
an armoring sheet intermediate portion connecting said front portion to said back portion in the longitudinal direction, and a left leg opening edge and a right leg opening edge opposing one another in a horizontal direction, said armoring sheet intermediate portion including a crotch portion wherein a horizontally extending crotch fold line extends and the armoring sheer is folded over on itself;
said left and right front side jointing edges being respectively joined to said left and right back side jointing edges so as to form left joined edges and right joined edges and define a waist opening surrounded by said front and back waist portions and so as to form a pair of right and left leg openings respectively defined by said right leg opening edge and said left leg opening edge;
waist portion elastic members arranged around said waist opening;
a plurality of hip surrounding elastic members arranged at the front portion and the back portion extending in the horizontal direction and being vertically spaced apart; and
a plurality of curved elastic members, at each of the front portion and the back portion, extending from the left joined edges to the right joined edges and curving downward to pass over the crotch portion, said curved elastic members being arranged spaced apart from each other and without intersecting with each other, and said curved elastic members having starting/trailing ends connected at the left and right joined edges and said starting/trailing ends being disposed at a predetermined spacing substantially over a range from an upper portion of the left and right joined edges to a lower portion of the left and right joined edges;
said hip surrounding elastic members being fixed on said armoring sheet by adhesive disposed on peripheries of said hip surrounding elastic members;
said curved elastic members being disposed to cross and contact the hip surrounding elastic members at intersections and, in at least areas proximate said left and right joined edges and circumscribed by said curved elastic members crossing the hip surrounding elastic members, said curved elastic members are fixed to said armoring sheet only at said intersections by the adhesive disposed on the peripheries of said hip surrounding elastic members and without adhesive on peripheries of said curved elastic members at positions between the hip surrounding elastic members in said at least areas proximate said left and right joined edges and circumscribed by said curved elastic members crossing the hip surrounding elastic members;
the curved elastic members on said front portion extending to intersect said absorbent body side edges at an intersection angle on an acute angle side of no less than 20° and no more than 30°; and
the curved elastic member groups arranged on said back portion side extending to intersect said absorbent body side edges at an intersection angle on an acute angle side of no less than 35° and no more than 60°.

2. A pants type disposable diaper as set forth in claim 1, wherein said curved elastic members are arranged at least five each at the front portion and the back portion.

3. A pants type disposable diaper as set forth in claim 1 or 2, wherein a closest one of the curved elastic members to said waist portion elastic members arranged on the front portion is spaced at a distance of 20 mm or less from a lowermost one of the waist portion elastic members on the front portion at said left and right joined edges.

4. A pants type disposable diaper as set forth in claim 3, wherein a closest one of the curved elastic members to said waist portion elastic members arranged on the back portion is spaced at a distance of 20 mm or less from lowermost one of the waist portion elastic members on the back portion at said left and right joined edges.

5. A pants type disposable diaper as set forth in claim 4, wherein an arrangement spacing of said curved elastic members in the left and right front jointing edges and the left and right back jointing edges are made substantially the same as an arrangement spacing of corresponding ones of said curved elastic members at the crotch portion, and wherein an elastic member of said curved elastic members positioned closest to the crotch fold line is spaced at a distance of ±50 mm or less from the crotch fold line.

6. A pants type disposable diaper as set forth in claim 4, wherein the curved elastic members arranged on said back portion are extended at the crotch portion toward the front portion so as to extend over the crotch fold line.

7. A pants type disposable diaper as set forth in claim 4, wherein the curved elastic members arranged at said from portion and said back portion are turned in arcuate curves at the crotch portion.

8. A pants type disposable diaper as set forth in claim 4, wherein said curved elastic members are cut and discontinued on said absorbent body.

9. A pants type disposable diaper as set forth in claim 8, wherein said curved elastic members are cut at positions substantially along the side edges of said absorbent body.

10. A pants type disposable diaper as set forth in claim 8, wherein said curved elastic members are fixed in an area whereat said absorbent body by an adhesive so applied at a vertical spacing to the armoring sheet as to form a plurality of rows along the horizontal direction, wherein the ratio between the spacing width of said adhesive and the spacing width in the adhesive spacing width direction between said curved elastic members is set substantially to an integral multiple, and wherein, on said absorbent body, said curved elastic members are cut and discontinued on lines along the longitudinal direction of the diaper.

11. A pants type disposable diaper as set forth in claim 8, wherein, on said absorbent, said hip surrounding elastic members are cut and discontinued.

12. A pants type disposable diaper as set forth in claim 8, wherein the curved elastic members arranged on said front portion and the curved elastic members arranged on said hack portion do not intersect at the crotch portion.

* * * * *